US009394162B2

(12) United States Patent
Rothberg et al.

(10) Patent No.: US 9,394,162 B2
(45) Date of Patent: *Jul. 19, 2016

(54) MICROFABRICATED ULTRASONIC TRANSDUCERS AND RELATED APPARATUS AND METHODS

(71) Applicant: Butterfly Network, Inc., Guilford, CT (US)

(72) Inventors: Jonathan M. Rothberg, Guilford, CT (US); Susan A. Alie, Stoneham, MA (US); Keith G. Fife, Palo Alto, CA (US); Nevada J. Sanchez, Guilford, CT (US); Tyler S. Ralston, Clinton, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/716,152

(22) Filed: May 19, 2015

(65) Prior Publication Data

US 2016/0009549 A1    Jan. 14, 2016

Related U.S. Application Data

(63) Continuation of application No. 14/635,197, filed on Mar. 2, 2015, now Pat. No. 9,067,779.

(60) Provisional application No. 62/024,179, filed on Jul. 14, 2014.

(51) Int. Cl.
*H01L 21/00* (2006.01)
*B81C 1/00* (2006.01)
*B06B 1/02* (2006.01)

(52) U.S. Cl.
CPC ........... *B81C 1/00238* (2013.01); *B06B 1/0292* (2013.01); *B81C 2203/0792* (2013.01); *H01L 2924/0002* (2013.01); *H01L 2924/146* (2013.01); *H01L 2924/1461* (2013.01)

(58) Field of Classification Search
CPC ................. H01L 2924/1461; H01L 2924/146; H01L 2924/1423
See application file for complete search history.

(56) References Cited

U.S. PATENT DOCUMENTS

| 5,286,671 A | 2/1994 | Kurtz et al. |
| 6,430,109 B1 | 8/2002 | Khuri-Yakub et al. |

(Continued)

FOREIGN PATENT DOCUMENTS

| GB | 2 467 776 A | 8/2010 |
| KR | 10-2013-0134724 A | 12/2013 |

(Continued)

OTHER PUBLICATIONS

International Search Report and Written Opinion mailed Jul. 1, 2014 for Application No. PCT/US2014/014705.

(Continued)

*Primary Examiner* — Su C Kim
(74) *Attorney, Agent, or Firm* — Wolf, Greenfield & Sacks, P.C.

(57) ABSTRACT

Micromachined ultrasonic transducers integrated with complementary metal oxide semiconductor (CMOS) substrates are described, as well as methods of fabricating such devices. Fabrication may involve two separate wafer bonding steps. Wafer bonding may be used to fabricate sealed cavities in a substrate. Wafer bonding may also be used to bond the substrate to another substrate, such as a CMOS wafer. At least the second wafer bonding may be performed at a low temperature.

16 Claims, 26 Drawing Sheets

(56) References Cited

U.S. PATENT DOCUMENTS

| | | |
|---|---|---|
| 6,443,901 B1 | 9/2002 | Fraser |
| 6,645,145 B1 | 11/2003 | Dreschel et al. |
| 6,659,954 B2 | 12/2003 | Robinson |
| 6,694,817 B2 | 2/2004 | Degertekin et al. |
| 6,779,387 B2 | 8/2004 | Degertekin |
| 6,795,374 B2 | 9/2004 | Barnes et al. |
| 6,831,394 B2 | 12/2004 | Baumgartner et al. |
| 6,865,140 B2 | 3/2005 | Thomenius et al. |
| 6,958,255 B2 | 10/2005 | Khuri-Yakub et al. |
| 7,030,536 B2 | 4/2006 | Smith et al. |
| 7,037,746 B1 | 5/2006 | Smith et al. |
| 7,052,464 B2 | 5/2006 | Wodnicki |
| 7,104,129 B2 | 9/2006 | Nasiri et al. |
| 7,125,383 B2 | 10/2006 | Hoctor et al. |
| 7,247,246 B2 | 7/2007 | Nasiri et al. |
| 7,250,353 B2 | 7/2007 | Nasiri et al. |
| 7,257,051 B2 | 8/2007 | Thomenius et al. |
| 7,285,897 B2 | 10/2007 | Fisher et al. |
| 7,312,440 B2 | 12/2007 | Degertekin et al. |
| 7,313,053 B2 | 12/2007 | Wodnicki |
| 7,375,420 B2 | 5/2008 | Fisher et al. |
| 7,441,321 B2 | 10/2008 | Baumgartner et al. |
| 7,441,447 B2 | 10/2008 | Degertekin et al. |
| 7,442,570 B2 | 10/2008 | Nasiri et al. |
| 7,451,651 B2 | 11/2008 | Woychik et al. |
| 7,518,251 B2 | 4/2009 | Fisher et al. |
| 7,530,952 B2 | 5/2009 | Huang et al. |
| 7,545,012 B2 | 6/2009 | Smith et al. |
| 7,557,342 B2 | 7/2009 | Federov et al. |
| 7,564,172 B1 | 7/2009 | Huang |
| 7,612,483 B2 | 11/2009 | Degertekin |
| 7,612,635 B2 | 11/2009 | Huang |
| 7,615,834 B2 | 11/2009 | Khuri-Yakub et al. |
| 7,622,848 B2 | 11/2009 | Lee et al. |
| 7,637,149 B2 | 12/2009 | Degertekin et al. |
| 7,646,133 B2 | 1/2010 | Degertekin |
| 7,687,976 B2 | 3/2010 | Haider et al. |
| 7,745,248 B2 | 6/2010 | Park et al. |
| 7,759,839 B2 | 7/2010 | Huang |
| 7,764,003 B2 | 7/2010 | Huang |
| 7,779,696 B2 | 8/2010 | Huang |
| 7,846,102 B2 | 12/2010 | Kupnik et al. |
| 7,878,977 B2 | 2/2011 | Mo et al. |
| 7,880,565 B2 | 2/2011 | Huang |
| 7,888,709 B2 | 2/2011 | Lemmerhirt et al. |
| 7,892,176 B2 | 2/2011 | Wodnicki et al. |
| 7,956,510 B2 | 6/2011 | Huang |
| 8,004,373 B2 | 8/2011 | Huang |
| 8,008,105 B2 | 8/2011 | Huang |
| 8,008,835 B2 | 8/2011 | Degertekin |
| 8,018,301 B2 | 9/2011 | Huang |
| 8,076,821 B2 | 12/2011 | Degertekin |
| 8,105,941 B2 | 1/2012 | Huang |
| 8,120,229 B2 | 2/2012 | Huang |
| 8,203,912 B2 | 6/2012 | Roest et al. |
| 8,222,065 B1 | 7/2012 | Smeys et al. |
| 8,241,931 B1 | 8/2012 | Antoine et al. |
| 8,247,945 B2 | 8/2012 | Huang |
| 8,277,380 B2 | 10/2012 | Daft et al. |
| 8,309,428 B2 | 11/2012 | Lemmerhirt et al. |
| 8,315,125 B2 | 11/2012 | Lemmerhirt et al. |
| 8,327,521 B2 | 12/2012 | Dirksen et al. |
| 8,334,133 B2 | 12/2012 | Federov et al. |
| 8,345,508 B2 | 1/2013 | Wodnicki et al. |
| 8,345,513 B2 | 1/2013 | Huang |
| 8,363,514 B2 | 1/2013 | Huang |
| 8,372,011 B2 | 2/2013 | Degertekin |
| 8,398,554 B2 | 3/2013 | Degertekin |
| 8,399,278 B2 | 3/2013 | Lemmerhirt et al. |
| 8,402,831 B2 | 3/2013 | Kupnik et al. |
| 8,429,808 B2 | 4/2013 | Huang |
| 8,451,693 B2 | 5/2013 | Nikoozadeh et al. |
| 8,483,014 B2 | 7/2013 | Huang |
| 8,526,271 B2 | 9/2013 | Huang |
| 8,559,274 B2 | 10/2013 | Huang |
| 8,563,345 B2 | 10/2013 | Adler et al. |
| 8,647,279 B2 | 2/2014 | Daft et al. |
| 8,658,453 B2 | 2/2014 | Lemmerhirt et al. |
| 8,665,672 B2 | 3/2014 | Soeda et al. |
| 8,957,564 B1 | 2/2015 | Hiroe et al. |
| 9,061,318 B2 | 6/2015 | Rothberg et al. |
| 9,067,779 B1 | 6/2015 | Rothberg et al. |
| 9,242,275 B2 | 1/2016 | Rothberg et al. |
| 2005/0121734 A1 | 6/2005 | Degertekin et al. |
| 2005/0177045 A1 | 8/2005 | Degertekin et al. |
| 2005/0203397 A1 | 9/2005 | Degertekin |
| 2007/0167811 A1 | 7/2007 | Lemmerhirt et al. |
| 2007/0167812 A1 | 7/2007 | Lemmerhirt et al. |
| 2007/0180916 A1 | 8/2007 | Tian et al. |
| 2007/0215964 A1 | 9/2007 | Khuri-Yakub et al. |
| 2008/0194053 A1 | 8/2008 | Huang |
| 2008/0290756 A1 | 11/2008 | Huang |
| 2008/0296708 A1 | 12/2008 | Wodnicki et al. |
| 2008/0308920 A1 | 12/2008 | Wan |
| 2009/0122651 A1 | 5/2009 | Kupnik et al. |
| 2009/0134497 A1 | 5/2009 | Barth et al. |
| 2009/0148967 A1 | 6/2009 | Wodnicki et al. |
| 2009/0176375 A1 | 7/2009 | Benson et al. |
| 2009/0250729 A1 | 10/2009 | Lemmerhirt et al. |
| 2010/0027830 A1 | 2/2010 | Hsu et al. |
| 2010/0225200 A1 | 9/2010 | Kupnik et al. |
| 2011/0084570 A1 | 4/2011 | Soeda et al. |
| 2011/0115333 A1 | 5/2011 | Ezaki |
| 2011/0140224 A1 | 6/2011 | Kropelnicki et al. |
| 2011/0272693 A1 | 11/2011 | Kobayashi et al. |
| 2012/0074509 A1 | 3/2012 | Berg et al. |
| 2012/0129301 A1 | 5/2012 | Or-Bach et al. |
| 2012/0187508 A1 | 7/2012 | Adler et al. |
| 2012/0193719 A1* | 8/2012 | Or-Bach ............ H01L 21/6835 257/368 |
| 2012/0248554 A1 | 10/2012 | Klein et al. |
| 2013/0096433 A1 | 4/2013 | Lemmerhirt et al. |
| 2013/0116561 A1 | 5/2013 | Rothberg et al. |
| 2013/0161702 A1 | 6/2013 | Chen |
| 2013/0169110 A1 | 7/2013 | Jeong et al. |
| 2014/0057382 A1 | 2/2014 | Supino et al. |
| 2014/0217478 A1 | 8/2014 | Rothberg et al. |
| 2014/0219062 A1 | 8/2014 | Rothberg et al. |
| 2014/0264660 A1 | 9/2014 | Rothberg et al. |
| 2015/0084053 A1 | 3/2015 | Rothberg et al. |
| 2015/0251896 A1 | 9/2015 | Rothberg et al. |
| 2015/0298170 A1 | 10/2015 | Rothberg et al. |
| 2016/0009544 A1 | 1/2016 | Rothberg et al. |

FOREIGN PATENT DOCUMENTS

| | | |
|---|---|---|
| WO | WO 2009/107940 A2 | 9/2009 |
| WO | WO 2012/017978 A2 | 2/2012 |
| WO | WO 2014/151525 A2 | 9/2014 |

OTHER PUBLICATIONS

Invitation to Pay Additional Fees mailed Nov. 6, 2014 for Application No. PCT/US2014/025924.

International Search Report and Written Opinion mailed Feb. 18, 2015 for Application No. PCT/US2014/025924.

Office Communication mailed Feb. 13, 2015 for U.S. Appl. No. 14/172,383.

[No Author Listed], Sil-Via, TSI & Advanced Features. Silex Microsystems. http://www.silexmicrosystems.com/mems-foundry/sil-via-tsi-advanced-features/ [last accessed Jan. 6, 2015]. 4 pages.

Calmes et al., Highly Integrated 2-D Capacitive Micromachined Ultrasonic Transducers. 1999 IEEE Ultrason Symp. 1999;1163-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., Electrical Through-Wafer Interconnects with Sub-PicoFarad Parasitic Capacitance. 2001 Microelectromechan Syst Conf. Aug. 24, 2001;18-21.

Daft et al., Microfabricated ultrasonic transducers monolithically integrated with high voltage electronics. Proc Ultrason Symp. 2004;493-6.

(56) References Cited

OTHER PUBLICATIONS

Dixon-Warren, Overview of MEMS microphone technologies for consumer applications. MEMS J. Mar. 8, 2011. http://www.memsjournal.com/2011/03/overview-of-mems-microphone-technologies-for-consumer-applications.html [last accessed Feb. 19, 2014]. 10 pages.

Eccardt et al., Micromachined ultrasound transducers with improved coupling factors from a CMOS compatible process. Ultrasonics. Mar. 2000;38:774-80.

Eccardt et al., Surface micromachined ultrasound transducer in CMOS technology. Proc Ultrason Symp. 1996;959-62.

Gurun et al., Front-end CMOS electronics for monolithic integration with CMUT arrays: circuit design and initial experimental results. Proc Ultrason Symp. 2008;390-3.

Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80.doi: 10.1109/ULTSYM.2012.0019.

Knight et al., Low Temperature Fabrication of Immersion Capacitive Micromachined Ultrasonic Transducers on Silicon and Dielectric Substrates. IEEE Trans Ultrason Ferroelectr Freq Contr. Oct. 2004;51(10):1324-33.

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

Lin et al., Packaging of Large and Low-Pitch Size 2D Ultrasonic Transducer Arrays. MEMS Conf. 2010;508-11.

Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.

Noble et al., A cost-effective and manufacturable route to the fabrication of high-density 2D micromachined ultrasonic transducer arrays and (CMOS) signal conditioning electronics on the same silicon substrate. Proc Ultrason Symp. 2001;941-5.

Noble et al., Low-temperature micromachined CMUTs with fully-integrated analogue front-end electronics. Proc Ultrason Symp. 2002;1045-50.

Oralkan et al., Volumetric Imaging Using 2D Capacitive Micromachined Ultrasonic Transducer Arrays (CMUTs): Initial Results. 2002 IEEE Ultrason Symp. 2002;1083-6.

Oralkan et al., Volumetric Ultrasound Imaging Using 2-D CMUT Arrays. IEEE Trans Ultrason Ferroelectr Freq Contr. Nov. 2003;50(11):1581-94.

Park et al., Fabrication of Capacitive Micromachined Ultrasonic Transducers via Local Oxidation and Direct Wafer Bonding. J Microelectromechan Syst. Feb. 2011;20(1):95-103.

Torkkeli et al., Capacitative microphone with low-stress polysilicon membrane and high-stress polysilicon backplate. Sensors and Actuators. 2000;85:116-23.

Tsuji et al., Low Temperature Process for CMUT Fabrication with Wafer Bonding Technique. IEEE Intl Ultrason Symp Proc. 2010;551-4.

Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference. Feb. 12, 2014;426-8.

Wodnicki et al., Multi-Row Linear CMUT Array Using CMUTs and Multiplexing Electronics. Proc Ultrason Symp. 2009;2696-9.

Wolffenbuttel et al., Low-temperature silicon wafer-to-wafer bonding using gold at eutectic temperature. Sensors and Actuators A. 1994;43:223-9.

Wygant et al., Integration of 2D CMUT Arrays with Front-End Electronics for Volumetric Ultrasound Imaging. IEEE Trans Ultrason Ferroelectr Freq Contr. Feb. 2008;55(2):327-42.

Zahorian et al., Single chip CMUT arrays with integrated CMOS electronics: fabrication process development and experimental results. Proc Ultrason Symp. 2008;386-9.

Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.

International Search Report and Written Opinion mailed Jun. 29, 2015 for Application No. PCT/US2015/026290.

Office Communication mailed May 21, 2015 for U.S. Appl. No. 14/208,351.

Office Communication mailed May 15, 2015 for U.S. Appl. No. 14/635,197.

Doody et al., Modeling and Characterization of CMOS-Fabricated Capacitive Micromachined Ultrasound Transducers. J Microelectromech Sys. Feb. 1, 2011;20(1):104-18.

Helin et al., Poly-SiGe-based CMUT array with high acoustical pressure. MEMS. 2012 IEEE 25th International Conference on Micro Electro Mechanical Systems. Jan. 29, 2012;305-8.

Lemmerhirt et al., A 32×32 capacitive micromachined ultrasonic transducer array manufactured in standard CMOS. IEEE Trans Ultrason Ferroelectr Freq Control. Jul. 2012;59(7):1521-36. doi: 10.1109/TUFFC.2012.2352.

Lemmerhirt et al., An electronically-scanned CMUT-in-CMOS transducer for hemodialysis vascular access monitoring. Ultrason Symp. 2011 IEEE International Conference. Oct. 18, 2011;2193-6.

Lu et al., Investigation of thermal stress influence on CMUT in standard CMOS process. Info Auto. 2009 ICIA International Conference. Jun. 22, 2009;1447-51.

Xu et al., Characterization of improved Capacitive Micromachined Ultrasonic Transducers (CMUTS) using ALD high- [Kappa] dielectric isola. MEMS. 2014 IEEE 27th International Conference on Micro Electro Mechanical Systems. Jan. 26, 2014;584-7.

Yu et al., Dual-bottom-electrode CMUT based on standard CMOS process. NEMS. 2001 IEEE International Conference. Feb. 20, 2011;21-4.

International Preliminary Report on Patentability mailed Aug. 20, 2015 for Application No. PCT/US2014/014705.

International Preliminary Report on Patentability mailed Sep. 24, 2015 for Application No. PCT/US2014/025924.

International Search Report and Written Opinion mailed Oct. 29, 2015 for Application No. PCT/US2015/040342.

Notice of Allowance mailed Dec. 4, 2015 for U.S. Appl. No. 14/172,383.

Notice of Allowance mailed Sep. 14, 2015 for U.S. Appl. No. 14/208,351.

Notice of Allowance mailed Nov. 10, 2015 for U.S. Appl. No. 14/711,145.

Cha et al., Influences of perforation ratio in characteristics of capacitive micromachined ultrasonic transducers in air. Sensors Actuators A. 2011;171:191-8.

Manzanares et al., Air-coupled MUMPs capacitive micromachined ultrasonic transducers with resonant cavities. Ultrason. 2012;52:482-9.

Zhuang et al., Integration of trench-isolated through-wafer interconnects with 2d capacitive micromachined ultrasonic transducer arrays. Sensors Actuators A. 2007;138:221-9.

\* cited by examiner

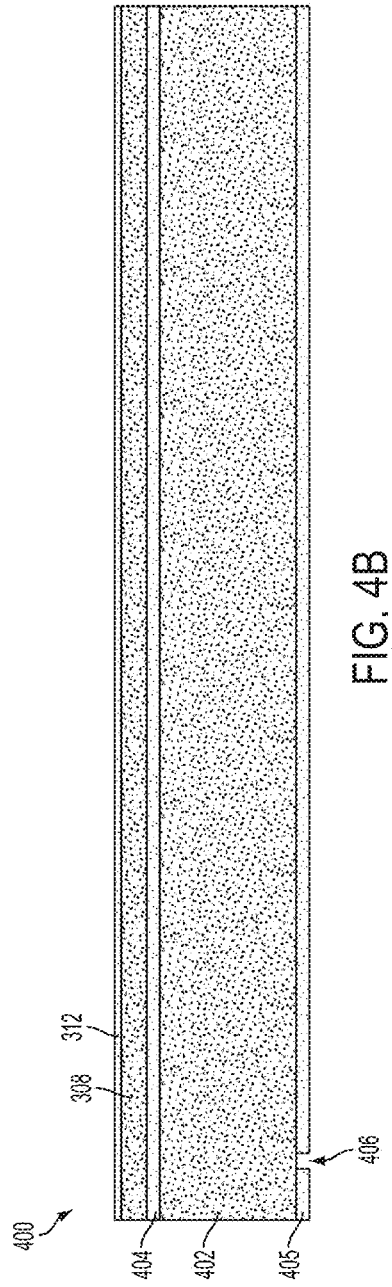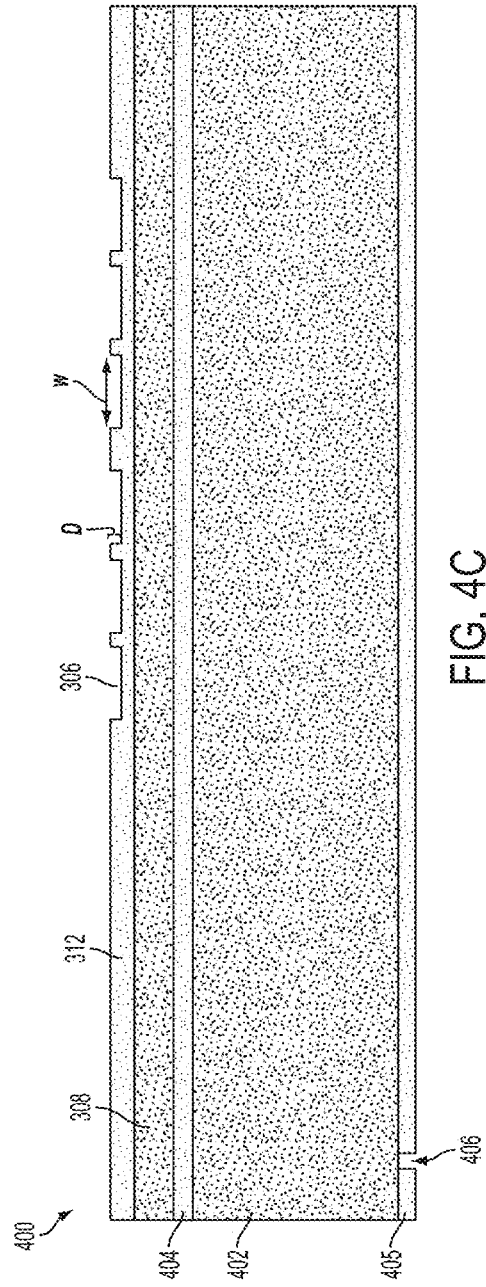

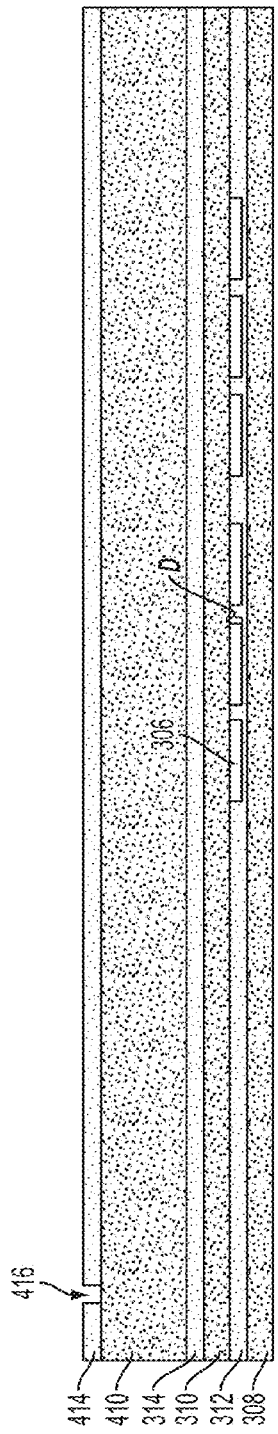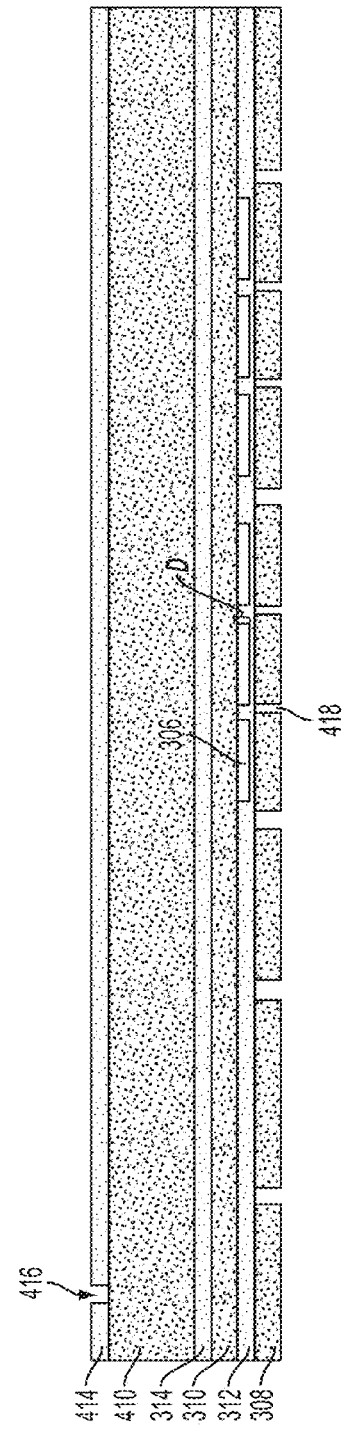

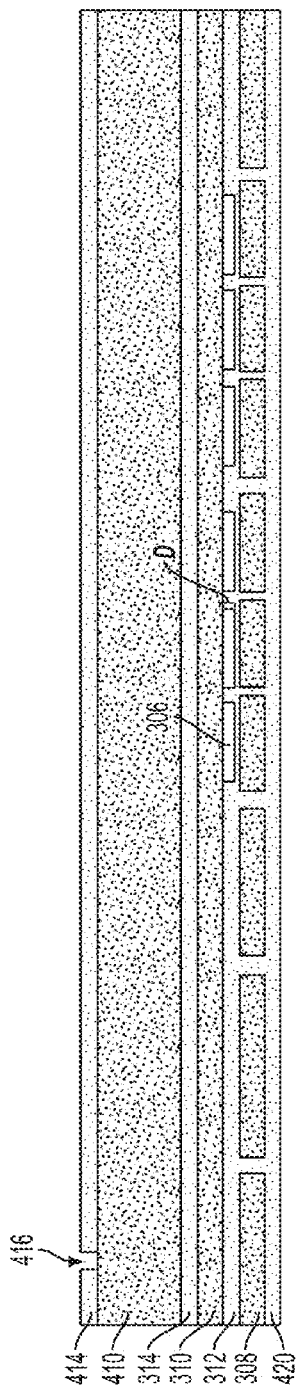
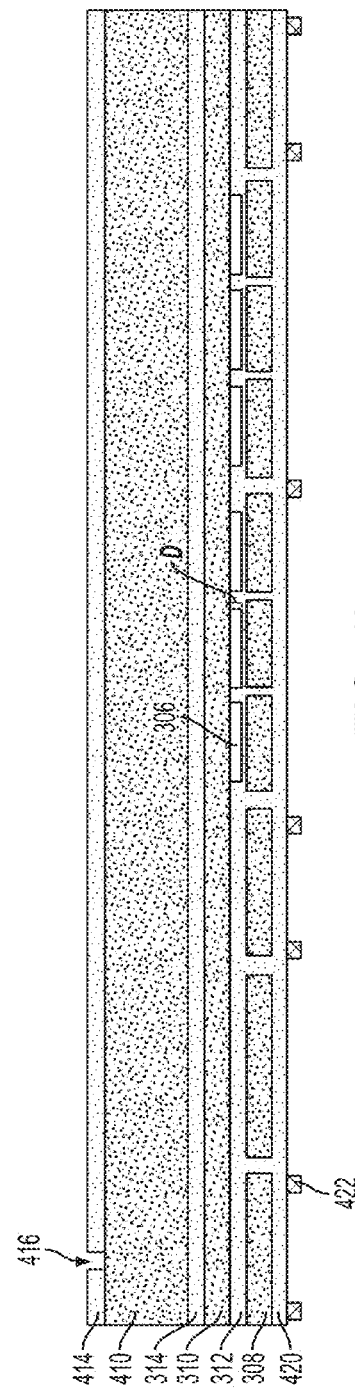
FIG. 4H
FIG. 4I

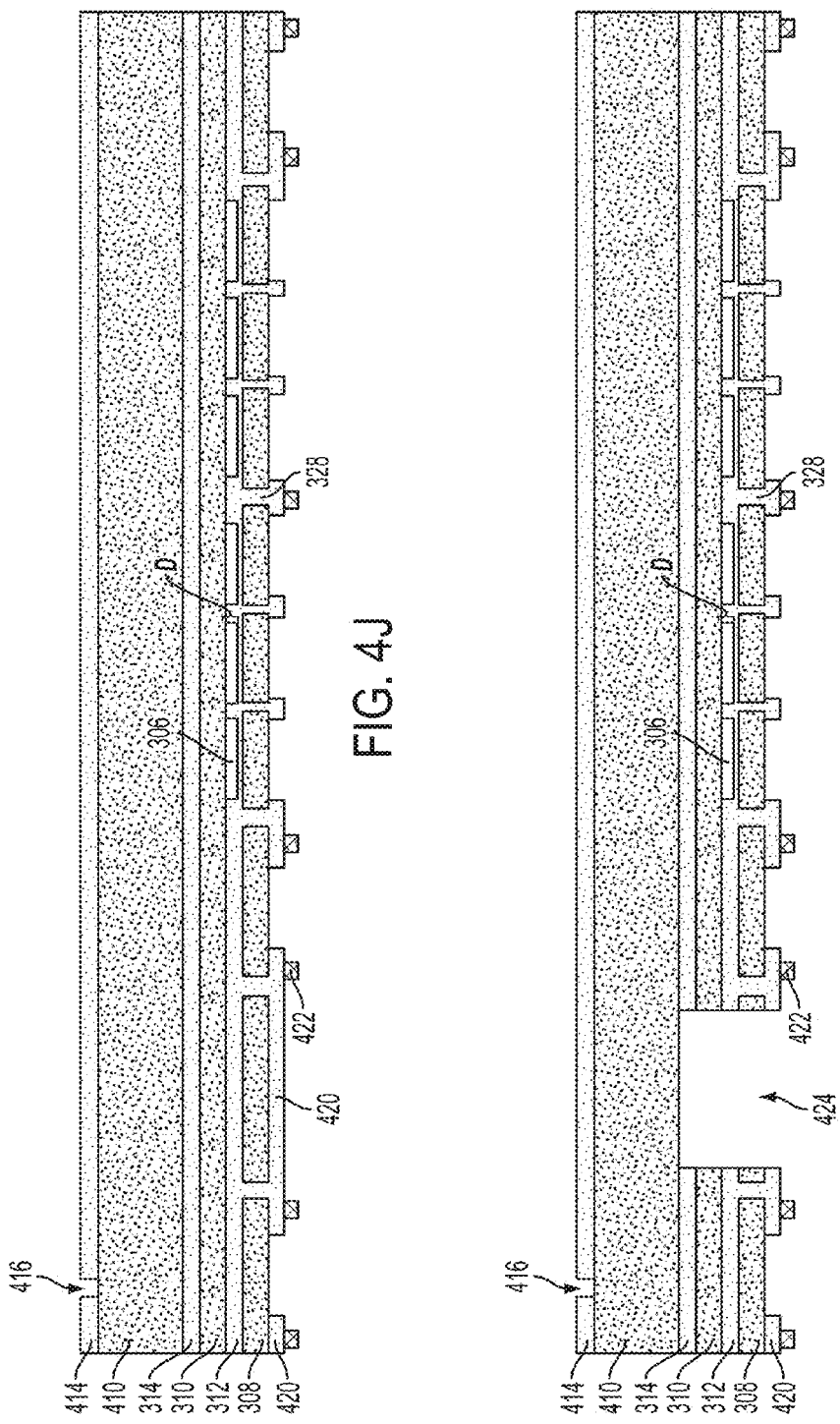

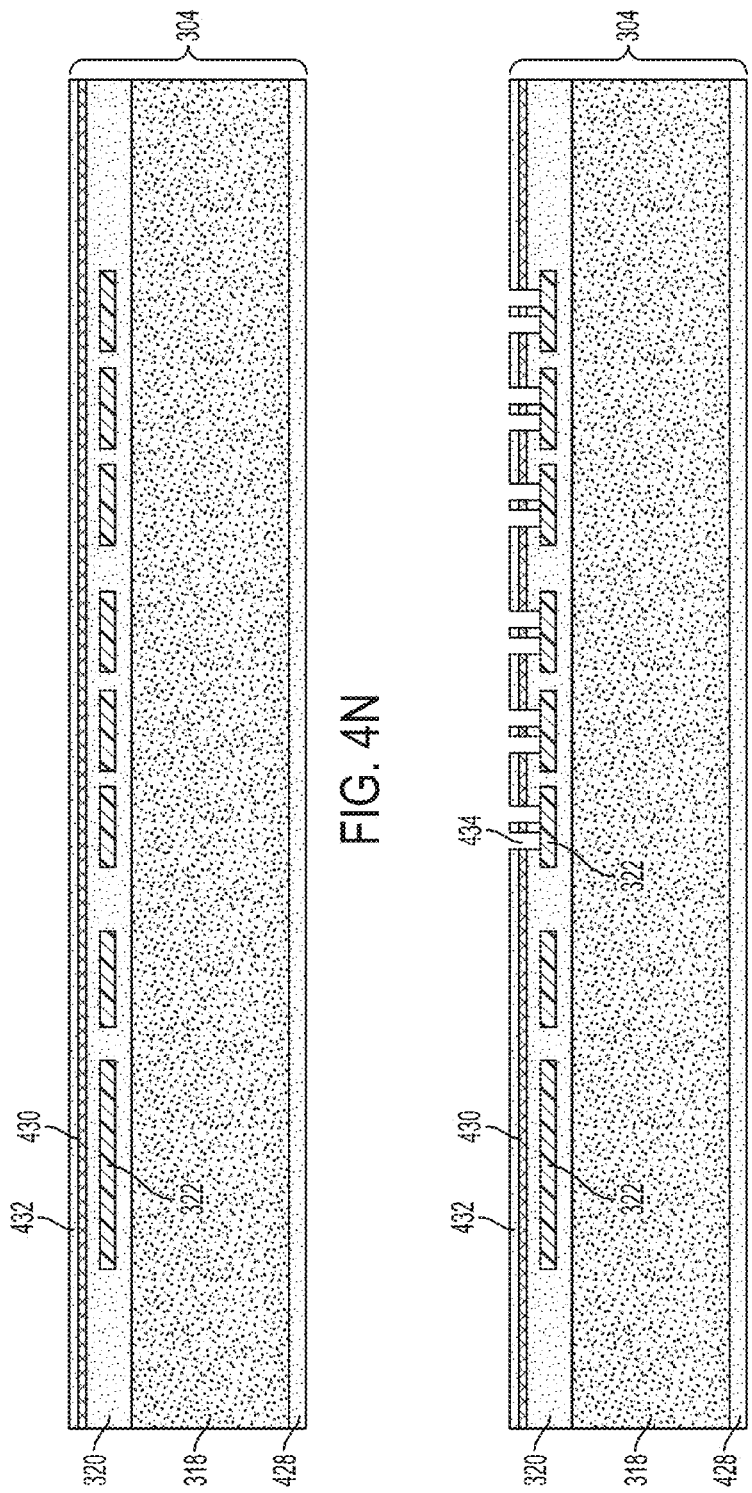

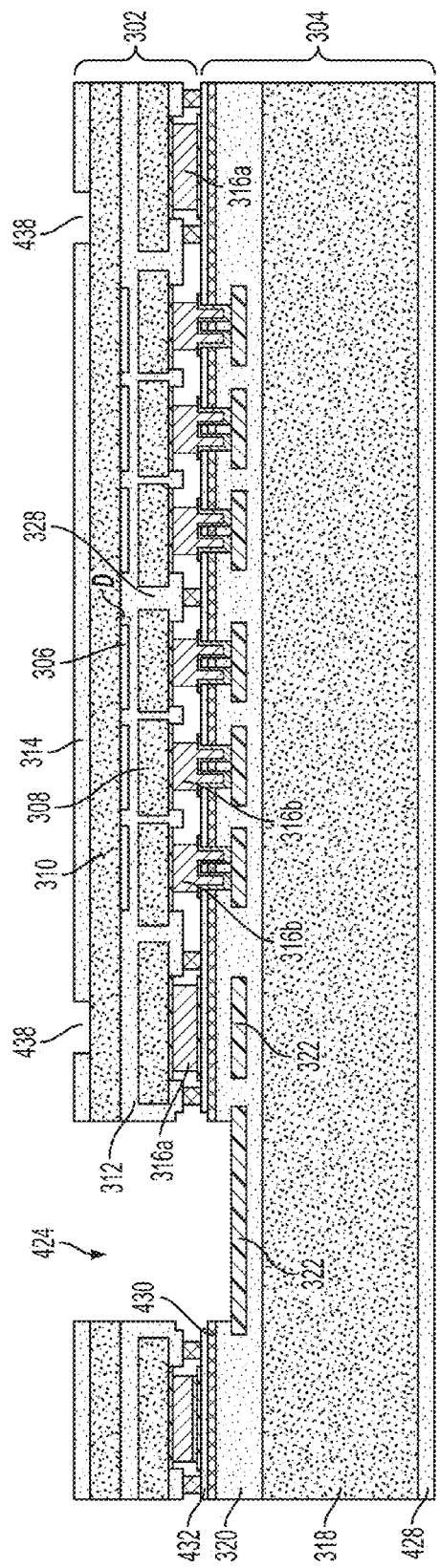

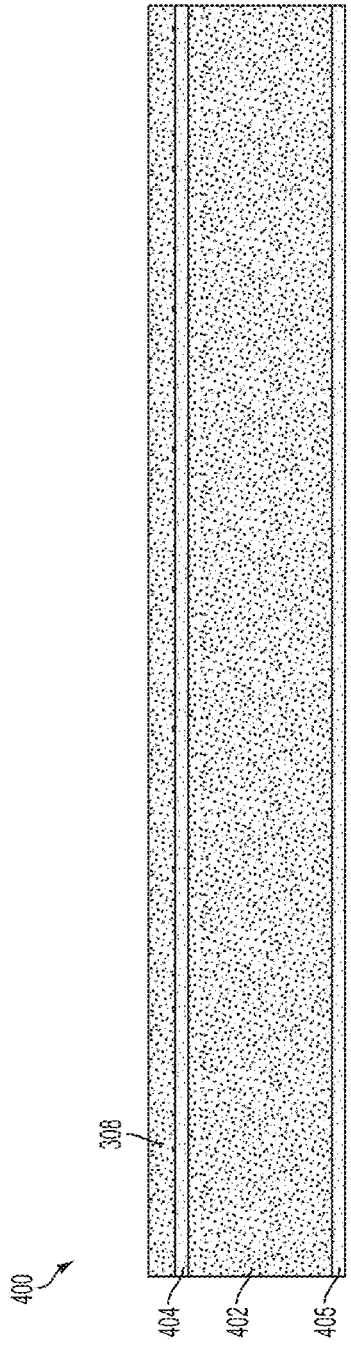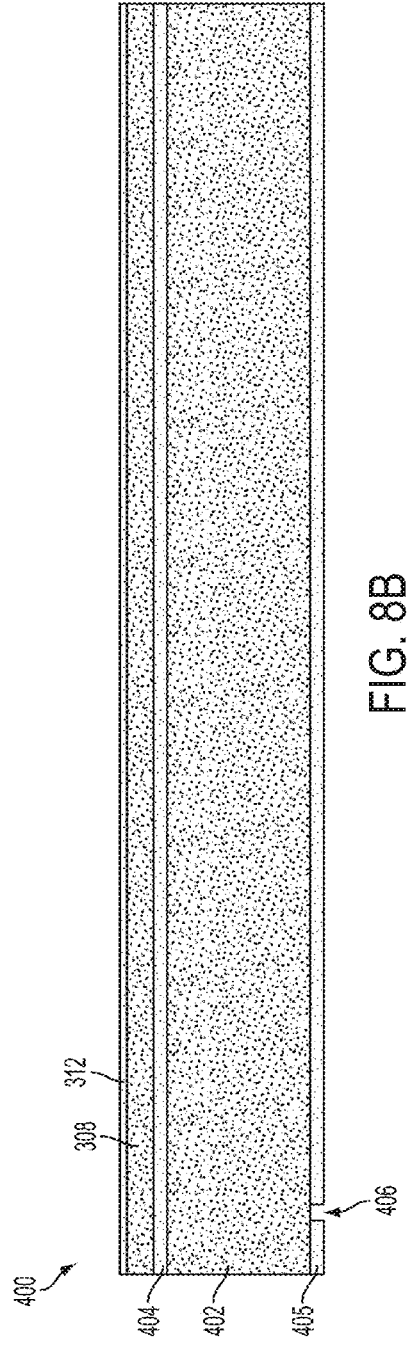

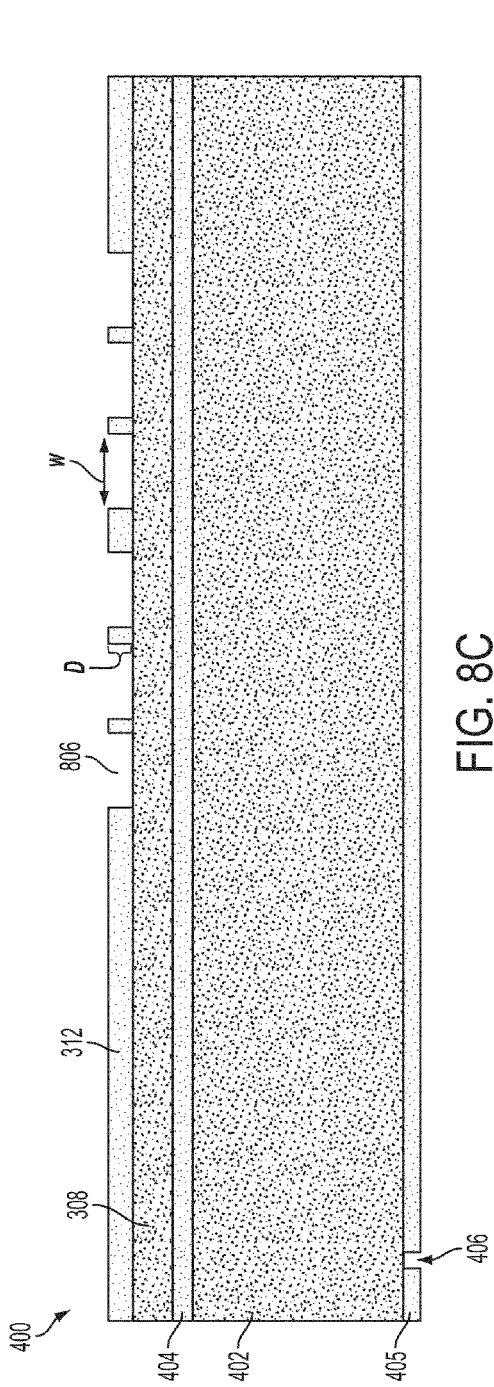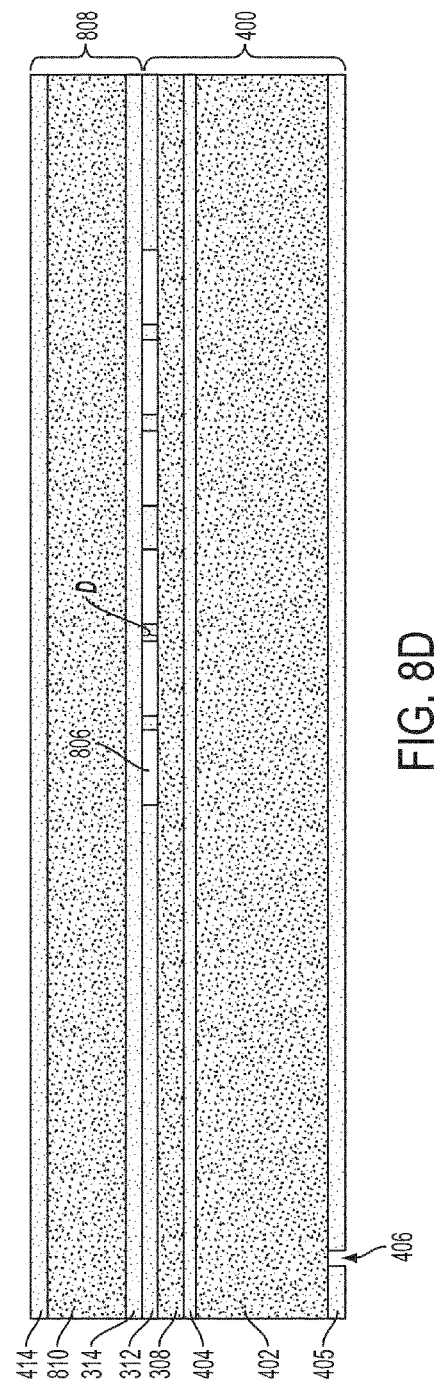

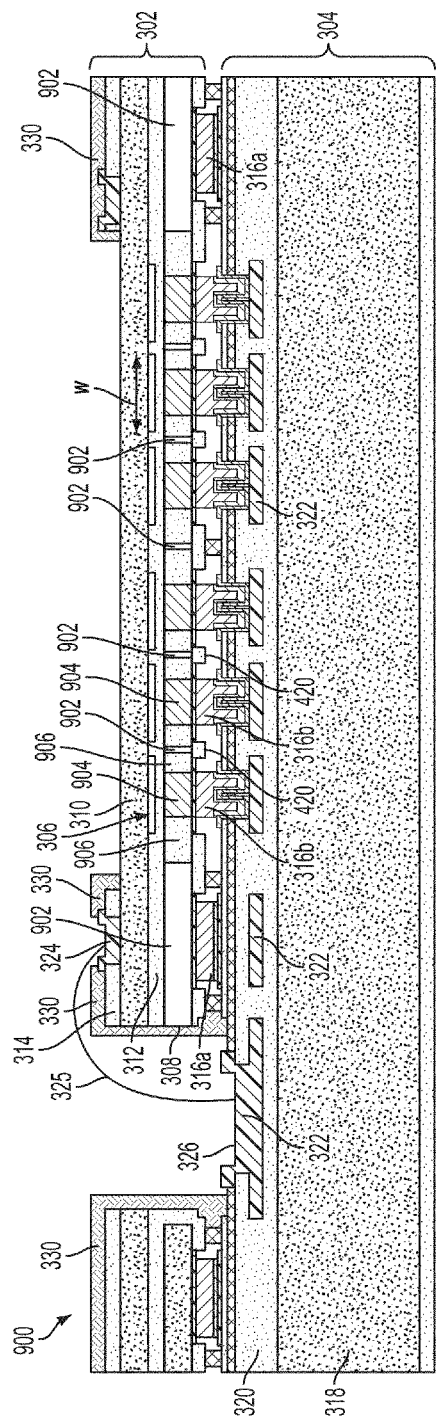
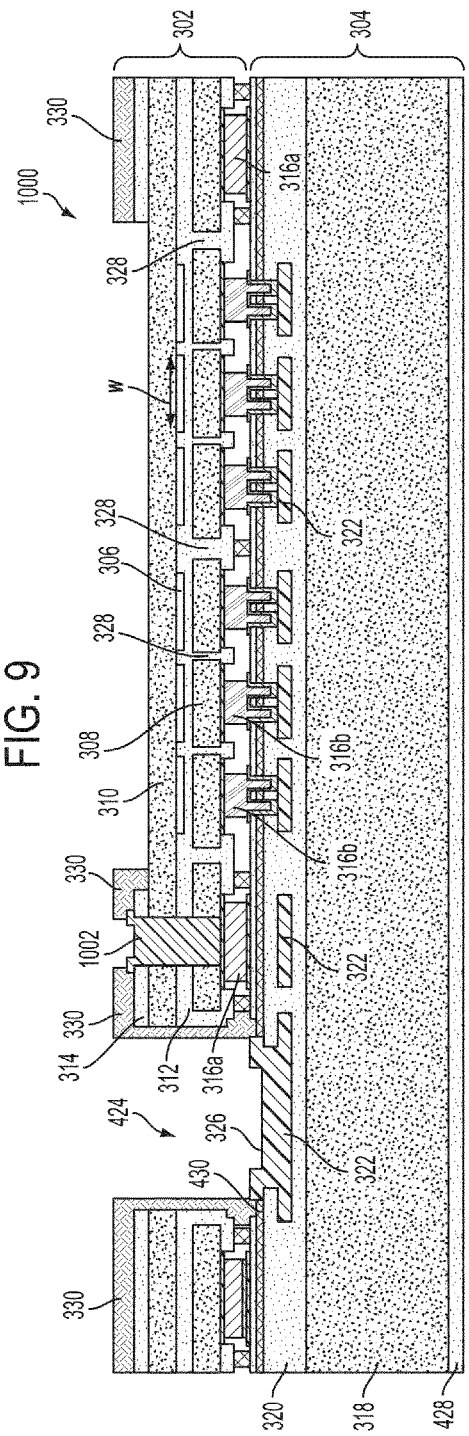
FIG. 9
FIG. 10

MICROFABRICATED ULTRASONIC TRANSDUCERS AND RELATED APPARATUS AND METHODS

CROSS REFERENCE TO RELATED APPLICATIONS

This application is a continuation, claiming the benefit under 35 U.S.C. §120, of U.S. patent application Ser. No. 14/635,197 entitled "Microfabricated Ultrasonic Transducers and Related Apparatus and Methods," filed Mar. 2, 2015, which is incorporated herein by reference in its entirety.

U.S. patent application Ser. No. 14/635,197 claims the benefit under 35 U.S.C. §119(e) of U.S. Provisional Patent Application Ser. No. 62/024,179 filed Jul. 14, 2014, and entitled "Microfabricated Ultrasonic Transducers and Related Apparatus and Methods," which is incorporated herein by reference in its entirety.

BACKGROUND

1. Field

The technology described herein relates to complementary metal oxide semiconductor (CMOS) transducers and methods for forming the same.

2. Related Art

Capacitive Micromachined Ultrasonic Transducers (CMUTs) are known devices that include a membrane above a micromachined cavity. The membrane may be used to transduce an acoustic signal into an electric signal, or vice versa. Thus, CMUTs can operate as ultrasonic transducers.

Two types of processes can be used to fabricate CMUTs. Sacrificial layer processes form the membrane of the CMUT on a first substrate above a sacrificial layer. Removal of the sacrificial layer results in the membrane being suspended above a cavity. Wafer bonding processes bond two wafers together to form a cavity with a membrane.

BRIEF SUMMARY

Aspects of the present application relate to fabrication and integration of CMUTs with CMOS wafers, thereby forming CMOS ultrasonic transducers (CUTs). According to an aspect of the present application, a wafer-level process is presented involving two wafer bonding steps. A first wafer bonding step may form sealed cavities by bonding together two silicon-on-insulator (SOI) wafers, the resulting bonded structure being considered an engineered substrate. Relatively high temperatures may be used, for example during an anneal, to facilitate achieving a strong bond. A handle layer of one of the two SOI wafers of the engineered substrate may then be removed, after which a second wafer bonding step may be performed to bond the engineered substrate with a CMOS wafer having integrated circuits (ICs) formed thereon. The second wafer bonding step may use a relatively low temperature to avoid damage to the ICs on the CMOS wafer. The handle layer of the second SOI wafer of the engineered substrate may then be removed, leaving a membrane over the cavities of the engineered substrate. Electrical connections between the CMOS IC and the engineered substrate allow for controllable ultrasonic transducers to be realized.

The wafer-level process described above may produce an ultrasound device with integrated CMUTs and CMOS ICs. The cavities of the CMUTs may be formed between two silicon layers representing the silicon device layers of the two SOI wafers used to form the engineered substrate. Yet, the handle layers of the two SOI wafers may be absent in the completed device, which facilitates achieving thin device dimensions and therefore a small size, among other benefits. Thus, the process may, in some aspects, include suitable steps for removing the handle layers while allowing for bonding of the engineered substrate with the CMOS wafer. The use of thru-silicon vias (TSVs) may also be absent in the final device, with suitable alternative structures being used to provide electrical connection to the resulting ultrasonic transducers.

According to another aspect of the present application, a bulk silicon wafer may be used in place of one or both of the SOI wafers described above. In such an instance, rather than removing a handle layer of the wafer, the wafer may be thinned to a desired point, for example using an etch stop represented by a doped layer of the bulk silicon wafer or using a timed etch. Thus, substantially the same structure may be achieved using either SOI or bulk silicon wafers or a combination of the two.

Accordingly, an aspect of the present application provides a wafer-level process including a first wafer bonding step to form sealed cavities by bonding together an SOI wafer and a bulk silicon wafer with cavities between them, the resulting bonded structure being considered an engineered substrate. Relatively high temperatures may be used, for example during an anneal, to facilitate achieving a strong bond. The bulk silicon wafer may be thinned, after which a second wafer bonding step may be performed to bond the engineered substrate with a CMOS wafer having integrated circuits (ICs) formed thereon. The second wafer bonding step may use a relatively low temperature to avoid damage to the ICs on the CMOS wafer. The handle layer of the SOI wafer of the engineered substrate may then be removed, leaving a membrane over the cavities of the engineered substrate.

According to an aspect of the present application, a method is provided comprising forming a plurality of cavities in a layer of silicon oxide on a first silicon device layer of a first SOI wafer, bonding the first SOI wafer with a second SOI wafer and then annealing the first and second SOI wafers, and removing a handle layer and a buried oxide layer of the first SOI wafer. The method further comprises bonding the first silicon device layer to a third wafer having at least one metal layer formed thereon, and removing a handle layer of the second SOI wafer subsequent to bonding the first silicon device layer to the third wafer.

According to an aspect of the present application, a method is provided comprising forming an engineered substrate having a plurality of sealed cavities by bonding a first wafer having open cavities formed therein with a second wafer and then thinning the first wafer to a thickness less than approximately 30 microns. The method further comprises bonding the engineered substrate with a third wafer at a temperature not exceeding 450° C., and subsequent to bonding the engineered substrate with the third wafer, thinning the second wafer to a thickness less than approximately 30 microns. In some embodiments, the second wafer, or a portion thereof, is configured to function as a membrane of an ultrasonic transducer, and therefore its thickness after being thinned is suitable to allow vibration. By contrast, in such instances it may be desirable for the first wafer not to vibrate, and thus its thickness after being thinned may be sufficiently great to minimize or prevent vibration. In a further embodiment, both the first and second wafers may be configured to vibrate, for example at different frequencies, to create a multi-frequency transducer. For example, the first membrane may be configured to resonate at half the center frequency of the second membrane.

According to an aspect of the present application, a method is provided, comprising forming a layer of silicon oxide on a first silicon device layer of a first SOI wafer, the first SOI wafer including a handle layer, a buried oxide (BOX) layer, and the first silicon device layer having a backside proximate the handle layer and a front side distal the handle layer. The method further comprises forming a plurality of cavities in the layer of silicon oxide, and bonding a second SOI wafer with the first SOI wafer such that a second silicon device layer of the second SOI wafer contacts the layer of silicon oxide and seals the plurality of cavities in the layer of silicon oxide. The method further comprises annealing the first and second SOI wafers after bonding them together, the annealing utilizing a temperature above 500° C. The method further comprises removing the handle layer of the first SOI wafer, etching a plurality of trenches in the first silicon device layer defining a plurality of electrode regions of the first silicon device layer corresponding to the plurality of cavities, and filling the plurality of trenches with an insulating material. The method further comprises forming metal contacts on the backside of the first silicon device layer, at least some of the metal contacts corresponding to the plurality of electrode regions. The method further comprises bonding the first silicon device layer with a CMOS wafer having integrated circuitry formed therein using the metal contacts on the backside of the first silicon device layer to contact bonding points on the CMOS wafer, wherein bonding the first silicon device layer with the CMOS wafer is performed below 450° C. The method further comprises removing a handle layer of the second SOI wafer.

According to an aspect of the present application, an apparatus is provided, comprising a CMOS wafer having an integrated circuit formed therein, and a substrate monolithically integrated with the CMOS wafer and including fewer than three silicon layers. A first silicon layer of the substrate and a second silicon layer of the substrate are arranged with a plurality of cavities therebetween.

According to an aspect of the present application, an apparatus is provided, comprising a CMOS wafer having an integrated circuit formed therein, and a substrate monolithically integrated with the CMOS wafer, the substrate having a first side proximate the CMOS wafer and a second side distal the CMOS wafer. The substrate comprises, in order from the first side to the second side, a first silicon layer, a layer of silicon oxide directly contacting the first silicon layer and having a plurality of cavities formed therein, and a second silicon layer directly contacting the silicon oxide and forming a membrane for the plurality of cavities.

The term "SOI wafer" as used herein has its conventional meaning, including a handle layer, a buried oxide (BOX) layer, and a silicon device layer separated from the handle layer by the BOX layer.

The term "engineered substrate" as used herein refers to a substrate engineered to differ from a basic silicon wafer or standard SOI wafer. An engineered substrate may also be a "composite substrate" formed by combining multiple distinct elements (e.g., multiple distinct wafers).

Throughout this disclosure, the use of the term "approximately" includes "exactly" unless context dictates otherwise. For example, describing a distance as being less than approximately 10 microns is to be understood to include the scenario in which the distance is less than 10 microns.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 8A-8D illustrate a variation on part of the fabrication sequence of FIGS. 4A-4T, according to a non-limiting embodiment of the present application.

FIG. 9 illustrates an implementation of the device 300 of FIG. 3 in which patterned doping is used to define electrodes of an ultrasonic transducer, according to a non-limiting embodiment of the present application.

FIG. 10 illustrates a variation on the device 300 of FIG. 3 in which an embedded contact provides electrical connection to an ultrasonic transducer membrane, according to a non-limiting embodiment of the present application.

DETAILED DESCRIPTION

Figure 1:
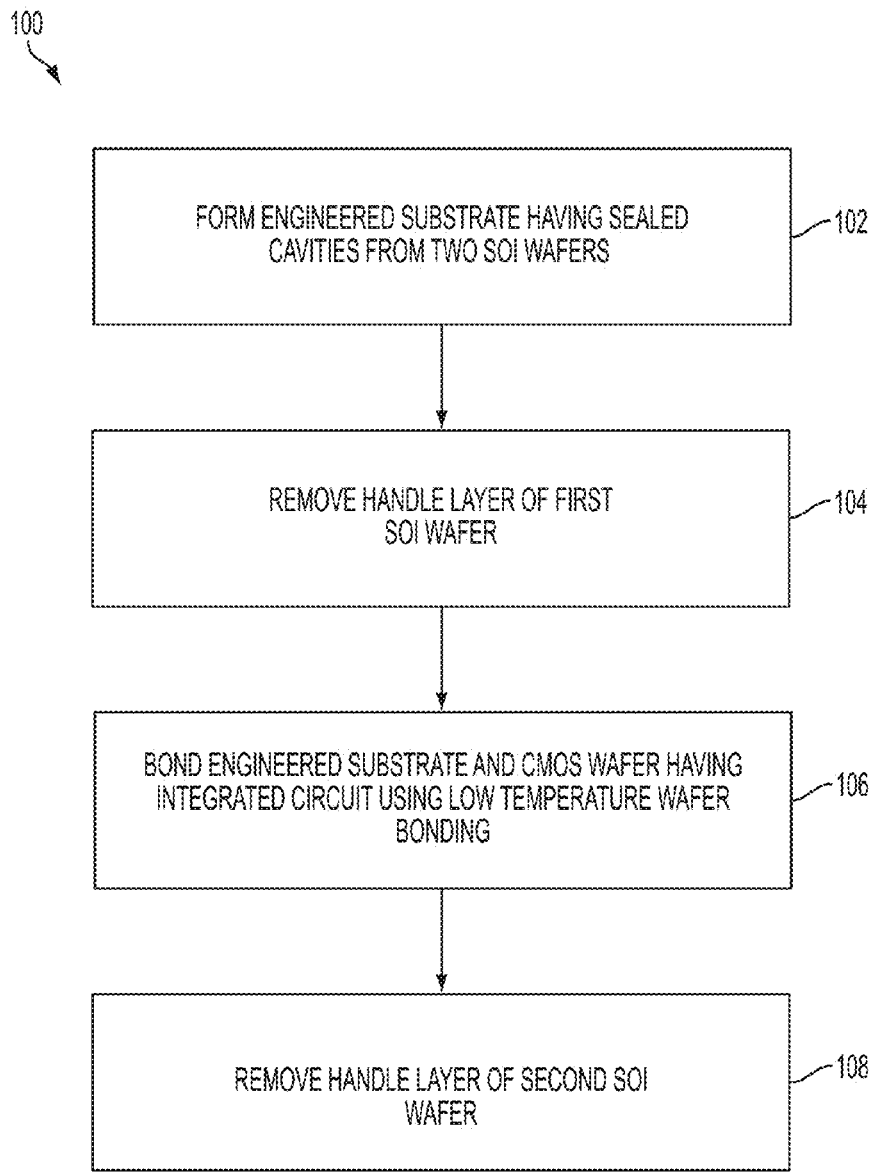
FIG. 1 is a flowchart of a fabrication sequence for fabricating an ultrasonic transducer integrated with a CMOS wafer, according to a non-limiting embodiment of the present application.

Aspects of the present application relate to fabrication and integration of CMUTs with CMOS wafers, thereby forming CMOS ultrasonic transducers (CUTs). The methods described provide scalable, low cost, high yield solutions to the challenge of integrating CMUTs with CMOS wafers using techniques available in commercial semiconductor foundries, thus utilizing a readily available supply chain. In some embodiments, piezoelectric micromachined ultrasonic transducers (PMUTs) are used instead of, or in addition to, CMUTs.

According to an aspect of the present application, a wafer-level process is presented involving two wafer bonding steps, at least one of which may take advantage of wafer level packaging techniques. A first wafer bonding step may form sealed cavities by bonding together two silicon-on-insulator (SOI) wafers, the resulting bonded structure being considered an engineered substrate, and representing a buried cavity SOI wafer. Relatively high temperatures may be used, for example during an anneal, to facilitate achieving a strong bond. A handle layer of one of the two SOI wafers of the engineered substrate may then be removed, after which a second wafer bonding step may be performed to bond the engineered substrate with a CMOS wafer having integrated circuits (ICs) formed thereon. The second wafer bonding step may use a relatively low temperature to avoid damage to the ICs on the CMOS wafer. The handle layer of the second SOI wafer of the engineered substrate may then be removed.

In some embodiments, the bonding used to form the engineered substrate with sealed cavities may include fusion bonding. In some such embodiments, the bonding may be performed at a low temperature. However, a relatively high temperature anneal may be performed to ensure a strong bond. The fabrication of sealed cavities is decoupled from the thermal budget of CMOS IC fabrication since the engineered substrate is fabricated prior to integrating such structures with a CMOS wafer, thus allowing for use of a relatively high temperature anneal without damaging ICs in the final device.

In some embodiments, the bonding performed to integrate the engineered substrate having sealed cavities with the CMOS wafer may include thermal compression (also referred to herein as "thermocompression"), eutectic bonding, or silicide bonding (which is a bond formed by bringing silicon of one substrate into contact with metal on a second substrate under sufficient pressure and temperature to form a metal silicide, creating a mechanical and electrical bond), as non-limiting examples. Such bonding may be performed at temperatures sufficiently low to avoid damage to the ICs on the CMOS wafer, while still providing for a strong bond and also facilitating electrical interconnection of the ICs on the CMOS wafer with the sealed cavities of the engineered substrate. Accordingly, aspects of the present application implement low temperature (e.g., below 450° C.) wafer bonding to form ultrasonic transducer membranes on CMOS wafers. Low temperature in this context may, in some embodiments, be below 450° C., below 400° C., below 350° C., between 200° C. and 450° C., any temperature within that range, or any suitable temperature for preserving structures on a CMOS wafer. Thus, the bonding processes as well as other fabrication steps for integrating the sealed cavities with CMOS ICs to form CUTs may avoid any anneals above 450° C.

According to an aspect of the present application, an apparatus including an engineered substrate is bonded with a CMOS wafer having a CMOS IC formed thereon. The engineered substrate may include multiple wafers bonded together to form sealed cavities. The engineered substrate may then be bonded with the CMOS wafer. The engineered substrate may include one substrate configured to serve as a membrane which vibrates and another substrate serving as a support, and which is not meant to vibrate. This latter substrate may be sufficiently thick (e.g., greater than approximately 5 microns) to prevent unwanted vibration, but also sufficiently thin (e.g., less than approximately 30 microns) to contribute to small device dimensions.

According to an aspect of the present application, an apparatus including an engineered substrate is bonded with a CMOS wafer having a CMOS IC formed thereon and the engineered substrate includes multiple wafers bonded together to form sealed cavities and configured to vibrate. One wafer of the engineered substrate may be configured to resonate at a first frequency and a second wafer of the engineered substrate may be configured to resonate at a different frequency. Thus, a multi-frequency ultrasound transducer may be created. One frequency may be used for transmit operations and the other for receive operations, as a non-limiting example. For example, a first, lower frequency may be used for transmit operations and a second, higher frequency (e.g., twice the frequency of the lower frequency) may be used for receive operations, as a non-limiting example.

The aspects and embodiments described above, as well as additional aspects and embodiments, are described further below. These aspects and/or embodiments may be used individually, all together, or in any combination of two or more, as the application is not limited in this respect.

As described, aspects of the present application provide a process for fabricating CUTs having integrated CMUTs and CMOS ICs and utilizing two separate bonding steps. The process may allow for a resulting structure to include a relatively thin engineered substrate having cavities formed between two silicon layers monolithically integrated with a CMOS wafer having CMOS ICs thereon. FIG. 1 illustrates an example of the process.

As shown, the method 100 may begin at stage 102 with the formation of an engineered substrate having sealed cavities. Two SOI wafers may be bonded together, for example with the silicon device layers of the two SOI wafers facing each other. One or both of the two SOI wafers may have a plurality of cavities formed therein, such that bonding the two SOI wafers together may result in sealed cavities suitable for use as the cavities of CMUTs. To ensure a strong bond between the two SOI wafers, high temperature processing may be used. For example, a high temperature anneal may be used subsequent to a low temperature wafer bond, such as a low temperature fusion bond. Thus, a combination of high and low temperatures may be used in forming the engineered substrate in some embodiments. High temperature in this context may, in some embodiments, be above 450° C., a temperature threshold above which CMOS ICs would typically be damaged.

The bonding of the two SOI wafers may be performed in vacuum so that the resulting sealed cavities have a low pressure (e.g., a pressure between approximately $1\times10^{-3}$ Torr and approximately $1\times10^{-5}$ Torr, a pressure less than approximately 1 atmosphere, or any other suitable pressure). In some embodiments, the bond is performed in an inert ambient, for example using $N_2$.

At stage 104, a handle layer of a first of the two SOI wafers may be removed, in any suitable manner, such as by a combination of grinding followed by etching. As a result, the engineered substrate may, at this point in the process, include three silicon layers: the silicon device layer of the first SOI wafer, the silicon device layer of the second SOI wafer, and the handle layer of the second SOI wafer. Although the silicon device layers of the SOI wafers may be thin, for example being 20 microns or less in thickness (e.g., 10 microns, 5 microns, 2.5 microns, 2 microns, 1 micron, or less, including any range or value within the range less than 20 microns), Applicants have appreciated that the handle layer of the second SOI wafer may provide sufficient structural support to allow for further processing of the engineered substrate.

At stage 106, the engineered substrate may be bonded with a CMOS wafer having integrated circuitry to form an integrated device. The bonding may be performed at temperatures below 450° C. to prevent damage to the circuitry of the CMOS wafer. In some embodiments, thermocompression bonding is used, although alternatives including eutectic bonding and silicide bonding are also possible, among others. The silicon device layer of the first SOI wafer may be arranged proximate the bonding surface of the CMOS wafer, for example by bonding a backside of the silicon device layer of the first SOI wafer with the CMOS wafer. Thus, the resulting structure may include, in order, a CMOS wafer, a first silicon device layer, a second silicon device layer of the second SOI wafer, and the handle layer of the second SOI wafer.

At stage 108, the handle layer of the second SOI wafer of the engineered substrate may be removed, in any suitable manner, for example by a combination of grinding followed by etching. As a result, in some embodiments, the engineered substrate may include only two silicon layers (the two silicon device layers of the SOI wafers used to form the engineered substrate) between which are the cavities. Having only two silicon layers may, among other benefits, facilitate achieving thin dimensions for the engineered substrate. For example, the engineered substrate at this stage may be relatively thin, for example being less than 100 microns in total thickness, less than 50 microns in total thickness, less than 30 microns in total thickness, less than 20 microns in total thickness, less than 10 microns in total thickness (e.g., approximately 8 microns or approximately 5 microns), or any other suitable thickness. Structures with such small thicknesses lack sufficient structural rigidity to survive many fabrication processes, including wafer bonding. Thus, according to some embodiments of the present application, the engineered substrate is not reduced to such dimensions until after bonding with the CMOS wafer, which can provide mechanical support to the engineered substrate. Moreover, as described further below in connection with FIG. 7, in some embodiments it is preferable for one of the two wafers of the engineered substrate to be sufficiently thick to minimize or prevent vibration of that wafer. Thus, while the engineered substrate may be thin, it may have a thickness of at least, for example, 4 microns in some embodiments, at least 5 microns in some embodiments, at least 7 microns in some embodiments, at least 10 microns in some embodiments, or other suitable thickness to prevent unwanted vibration.

Electrical connections may be made between the ICs on the CMOS wafer and the sealed cavities of the engineered substrate to provide functioning ultrasonic transducers. For example, the silicon device layer of the engineered substrate proximate the CMOS wafer may serve as a bottom electrode for the ultrasonic transducers while the silicon device layer distal the CMOS wafer may serve as a membrane, and electrical connections may be made to these structures as appropriate to control operation of the membrane (e.g., to actuate (or induce vibration of) the membrane by applying a voltage). In some embodiments, electrical connection may be made (or may be at least partially completed) by the bonding of stage 106. For example, bonding the engineered substrate with the CMOS wafer may involve using conductive bonding materials (e.g., metals) which serve as both bonding materials and electrical connections. Alternatively, or additionally, electrical connections may be made subsequent to bonding of the engineered substrate with the CMOS wafer. For example, bonding the engineered substrate with the CMOS wafer may form electrical connections to a bottom electrode of the ultrasonic transducer, and on-chip metal interconnect and/or wire bonds may be formed subsequently to provide electrical connection to top electrodes or membrane of the ultrasonic transducer.

Figure 2:
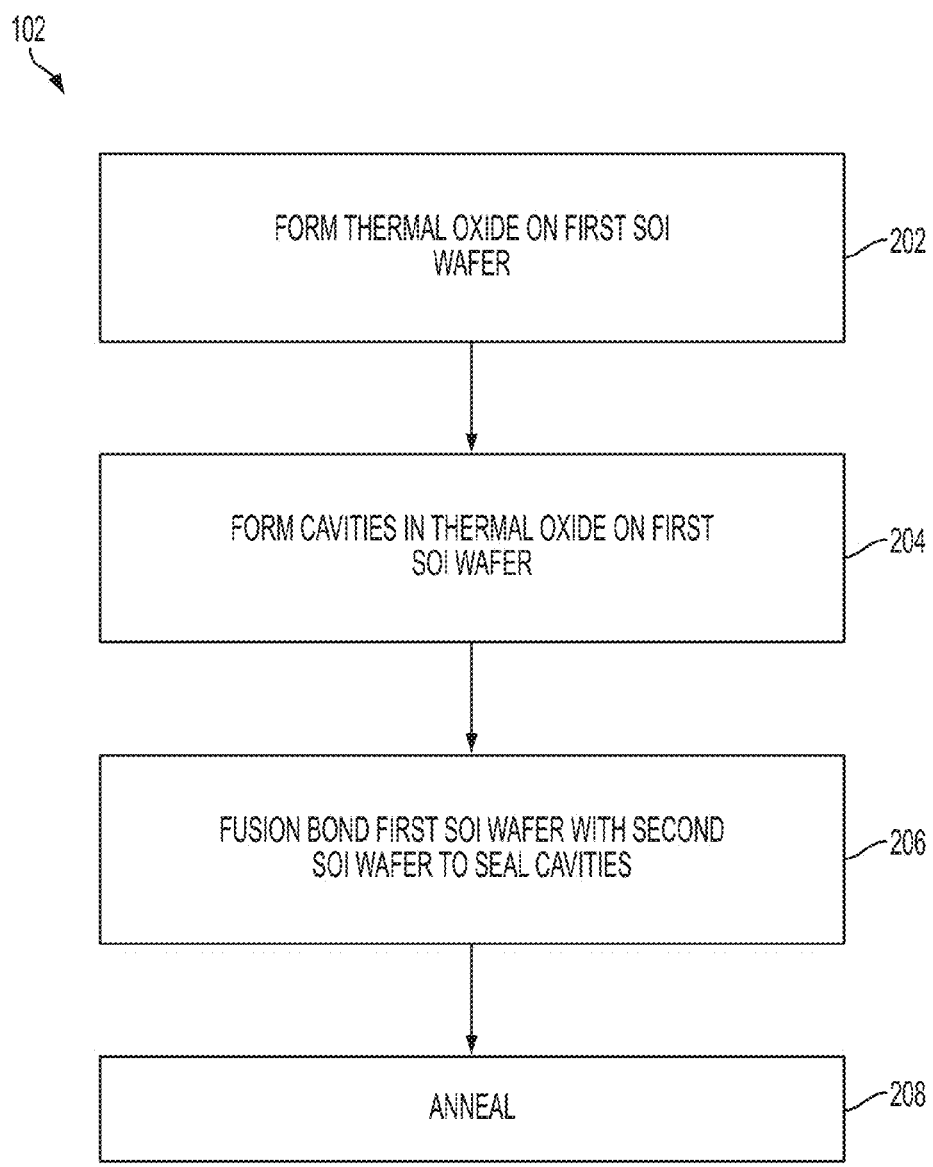
FIG. 2 is a flowchart illustrating a detailed example of a stage of the process 100 of FIG. 1.

FIG. 2 provides further detail with respect to an example of the implementation of stage 102 of method 100, although it should be appreciated that alternative manners for implementing stage 102 are possible. In the non-limiting example shown, the cavities of the engineered substrate may be formed by first forming cavities in a thermal oxide (an oxide formed by thermal oxidation) on a first of the two SOI wafers. That is, a first SOI wafer may include a handle layer (e.g., a handle silicon layer), a buried oxide (BOX) layer, and a silicon device layer, on which a thermal oxide may be formed at stage 202 by thermally oxidizing the silicon device layer. It should be appreciated that a thermal oxide represents a non-limiting example of an oxide, and that other types of oxides may alternatively be formed.

At stage 204, cavities may be formed in the thermal oxide of the first SOI wafer, for example by any suitable etching. In some embodiments, the cavities do not completely reach the silicon device layer, such that a (thin) layer of oxide defines the cavity boundaries. However, in other embodiments the cavities may extend to the surface of the silicon device layer or further. In some embodiments, the thermal oxide may be etched to the surface of the silicon device layer and then an additional layer of thermal oxide may be formed such that the cavities are defined by a layer of oxide.

At stage 206, the first SOI wafer, having the cavities formed in the thermal oxide thereon, may be bonded with a second SOI wafer, for example using a low temperature fusion bond. In some embodiments, the second SOI wafer includes a handle layer (e.g., a handle silicon layer), a BOX layer, and a silicon device layer, and the bonding involves making direct contact between the thermal oxide layer of the first SOI wafer and the silicon device layer of the second SOI wafer, thus forming a $Si-SiO_2$ bond. In an alternative embodiment, the second SOI wafer may include an oxide layer on the silicon device layer, such that bonding the first and second SOI wafers together may involve making direct contact with oxide layers of the two SOI wafers, thus forming a $SiO_2-SiO_2$ bond.

As a result of bonding the two SOI wafers together, the cavities in the first SOI wafer may be sealed. For example, the cavities may be vacuum sealed in some embodiments, although in other embodiments a vacuum seal may not be formed.

At stage 208, an anneal may be performed to facilitate formation of a strong bond between the two SOI wafers. As described previously, in some embodiments the anneal may be a high temperature anneal, for example being performed between approximately 500° C. and approximately 1,500° C. (e.g., 500° C., 750° C., 1,000° C., 1,250° C.), including any temperature or range of temperatures within that range (e.g., between approximately 500° C. and approximately 1,200° C.), although other temperatures may alternatively be used. In some embodiments, an anneal may be performed between approximately 300° C. and approximately 1,200° C.

Figure 3:
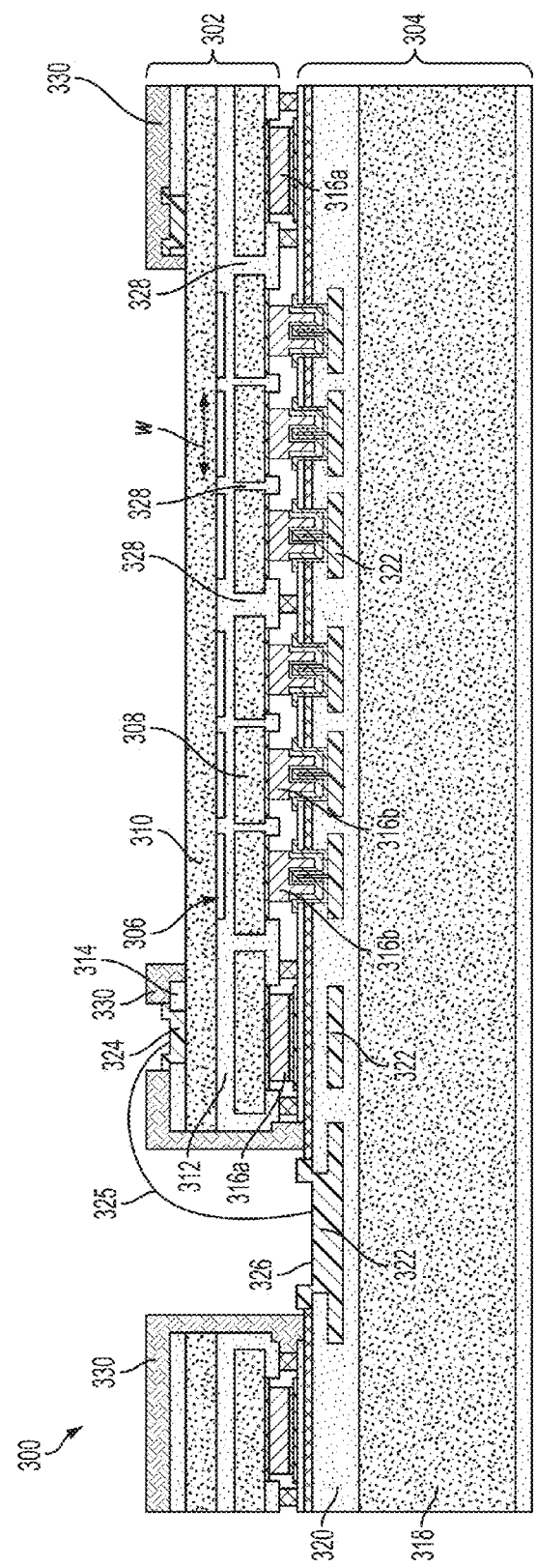
FIG. 3 is a cross-sectional view of a device including a CMOS wafer integrated with an engineered substrate having sealed cavities, according to a non-limiting embodiment of the present application.

FIG. 3 is a cross-sectional view of an ultrasound device including a CMOS wafer integrated with an engineered substrate having sealed cavities, according to a non-limiting embodiment of the present application. The device 300 may be formed by implementing the methods of FIGS. 1-2.

The device 300 includes an engineered substrate 302 integrated with a CMOS wafer 304. The engineered substrate 302 includes a plurality of cavities 306 formed between a first silicon device layer 308 and a second silicon device layer 310. A silicon oxide layer 312 (e.g., a thermal silicon oxide—a silicon oxide formed by thermal oxidation of silicon) may be formed between the first and second silicon device layers 308 and 310, with the cavities 306 being formed therein. In this non-limiting example, the first silicon device layer 308 may be configured as a bottom electrode and the second silicon device layer 310 may be configured as a membrane. Thus, the combination of the first silicon device layer 308, second silicon device layer 310, and cavities 306 may form an ultrasonic transducer (e.g., a CMUT), of which six are illustrated in this non-limiting cross-sectional view. To facilitate operation as a bottom electrode or membrane, one or both of the first silicon device layer 308 and second silicon device layer 310 may be doped to act as conductors, and in some cases are highly doped (e.g., having a doping concentration greater than $10^{15}$ dopants/cm$^3$ or greater).

The engineered substrate 302 may further include an oxide layer 314 on top of the second silicon device layer 310, which may represent the BOX layer of an SOI used to form the engineered substrate. The oxide layer 314 may function as a passivation layer in some embodiments and, as shown, may be patterned to be absent over the cavities 306. Contacts 324, described further below, and passivation layer 330 may be included on the engineered substrate. The passivation layer 330 may be patterned to allow access to one or more contacts 324, and may be formed of any suitable passivating material. In some embodiments, the passivation layer 330 is formed of $Si_3N_4$ and in some embodiments is formed by a stack of $SiO_2$ and $Si_3N_4$, although alternatives are possible.

The engineered substrate 302 and CMOS wafer 304 may be bonded together at bond points 316a and 316b. The bond points may represent eutectic bond points, for example formed by a eutectic bond of a layer on engineered substrate 302 with a layer on CMOS wafer 304, or may be any other suitable bond type described herein (e.g., a silicide bond or thermocompression bond). In some embodiments, the bond points 316a and 316b may be conductive, for example being formed of metal. The bond points 316a may function solely as bond points in some embodiments, and in some embodiments may form a seal ring, for example hermetically sealing the ultrasonic transducers of the device 300 as described further below in connection with FIG. 6. In some embodiments, the bond points 316a may define a seal ring that also provides electrical connection between the engineered substrate and CMOS wafer. Similarly, the bond points 316b may serve a dual purpose in some embodiments, for example serving as bond points and also providing electrical connection between the ultrasonic transducers of the engineered substrate 302 and the IC of the CMOS wafer 304. In those embodiments in which the engineered substrate is not bonded with a CMOS wafer, examples of which are described further below, the bond points 316b may provide electrical connection to any electrical structures on the substrate to which the engineered substrate is bonded.

The CMOS wafer 304 includes a base layer (e.g., a bulk silicon wafer) 318, an insulating layer 320, and a metallization 322. The metallization 322 may be formed of aluminum, copper, or any other suitable metallization material, and may represent at least part of an integrated circuit formed in the CMOS wafer. For example, metallization 322 may serve as a routing layer, may be patterned to form one or more electrodes, or may be used for other functions. In practice, the CMOS wafer 304 may include multiple metallization layers and/or post-processed redistribution layers, but for simplicity only a single metallization is illustrated.

The bond points 316b may provide electrical connection between the metallization 322 of CMOS wafer 304 and the first silicon device layer 308 of the engineered substrate. In this manner, the integrated circuitry of the CMOS wafer 304 may communicate with (e.g., send electrical signals to and/or receive electrical signals from) the ultrasonic transducer electrodes and/or membranes of the engineered substrate. In the illustrated embodiments, a separate bond point 316b is illustrated as providing electrical connection to each sealed cavity (and therefore for each ultrasonic transducer), although not all embodiments are limited in this manner. For example, in some embodiments, the number of electrical contacts provided may be less than the number of ultrasonic transducers.

Electrical contact to the ultrasonic transducer membranes represented by second silicon device layer 310 is provided in this non-limiting example by contacts 324, which may be formed of metal or any other suitable conductive contact material. In some embodiments, an electrical connection may be provided between the contacts 324 and the bond pad 326 on the CMOS wafer. For example, a wire bond 325 may be provided or a conductive material (e.g., metal) may be deposited over the upper surface of the device and patterned to form a conductive path from the contacts 324 to the bond pad 326. However, alternative manners of connecting the contacts 324 to the IC on the CMOS wafer 304 may be used. In some embodiments an embedded via may be provided from the first silicon device layer 308 to a bottom side of the second silicon device layer 310, thus obviating any need for the contacts 324 on the topside of the second silicon device layer 310. An example is described below in connection with FIG. 11. In such embodiments, suitable electrical isolation may be provided relative to any such via to avoid electrically shorting the first and second silicon device layers.

The device 300 also includes isolation structures (e.g., isolation trenches) 328 configured to electrically isolate groups of ultrasonic transducers (referred to herein as "ultrasonic transducer elements") or, as shown in FIG. 3, individual ultrasonic transducers. The isolation structures 328 may include trenches through the first silicon device layer 308 that are filled with an insulating material in some embodiments. Alternatively, the isolation structures 328 may be formed by suitable doping as described further below in connection with FIG. 9. Isolation structures 328 are optional.

Various features of the device 300 are now noted. For instance, it should be appreciated that the engineered substrate 302 and CMOS wafer 304 wafer may be monolithically integrated, thus providing for monolithic integration of ultrasonic transducers with CMOS ICs. In the illustrated embodiment, the ultrasonic transducers are positioned vertically (or stacked) relative to the CMOS IC, which may facilitate formation of a compact ultrasound device by reducing the chip area required to integrate the ultrasonic transducers and CMOS IC.

Additionally, the engineered substrate 302 includes only two silicon layers 308 and 310, with the cavities 306 being formed between them. The first silicon device layer 308 and second silicon device layer 310 may be thin, for example each being less than 50 microns in thickness, less than 30 microns in thickness, less than 20 microns in thickness, less than 10 microns in thickness, less than 5 microns in thickness, less than 3 microns in thickness, or approximately 2 microns in thickness, among other non-limiting examples. Such dimensions contribute to achieving a small device and may facilitate making electrical contact to the ultrasonic transducer membrane (e.g., second silicon device layer 310) without the need for TSVs. TSVs are typically complicated and costly to implement, and thus avoiding use of them may increase manufacturing yield and reduce device cost. Moreover, forming TSVs requires special fabrication tools not possessed by many commercial semiconductor foundries, and thus avoiding the need for such tools can improve the supply chain for forming the devices, making them more commercially practical than if TSVs were used.

The engineered substrate 302 as shown in FIG. 3 may be relatively thin, for example being less than 100 microns in total thickness, less than 50 microns in total thickness, less than 30 microns in total thickness, less than 20 microns in total thickness, less than 10 microns in total thickness, or any other suitable thickness. The significance of such thin dimensions has been described previously herein in terms of the lack of structural integrity and the inability to perform various types of fabrication steps (e.g., wafer bonding) with layers of such thin dimensions. Thus, it is noteworthy that such thin dimensions may be achieved in the device 300.

Also, the silicon device layers 308 and 310 may be formed of single crystal silicon. The mechanical and electrical properties of single crystal silicon are understood, and thus the use of such materials in an ultrasonic transducer (e.g., as the membrane of a CMUT) may facilitate design and control of the ultrasonic transducer behavior.

Another feature worth noting is that there is a gap between parts of the CMOS wafer 304 and the first silicon device layer 308 since the two are bonded at discrete bond points 316b rather than by a bond covering the entire surface of the CMOS wafer 304. The significance of this gap is that the first silicon device layer 308 may vibrate if it is sufficiently thin. Such vibration may be undesirable, for instance representing unwanted vibration in contrast to the desired vibration of the second silicon device layer 310. Accordingly, it is beneficial in at least some embodiments for the first silicon device layer 308 to be sufficiently thick to minimize or avoid such vibration.

In alternative embodiments, it may be desirable for both the first and second silicon device layers 308 and 310 to vibrate. For instance, they may be constructed to exhibit different resonance frequencies, thus creating a multi-frequency device. The multiple resonance frequencies (which may be related as harmonics in some embodiments) may be used, for example, in different operating states of an ultrasound transducer. For example, the first silicon device layer 308 may be configured to resonant at half the center frequency of the second silicon device layer 310.

Figure 4A:
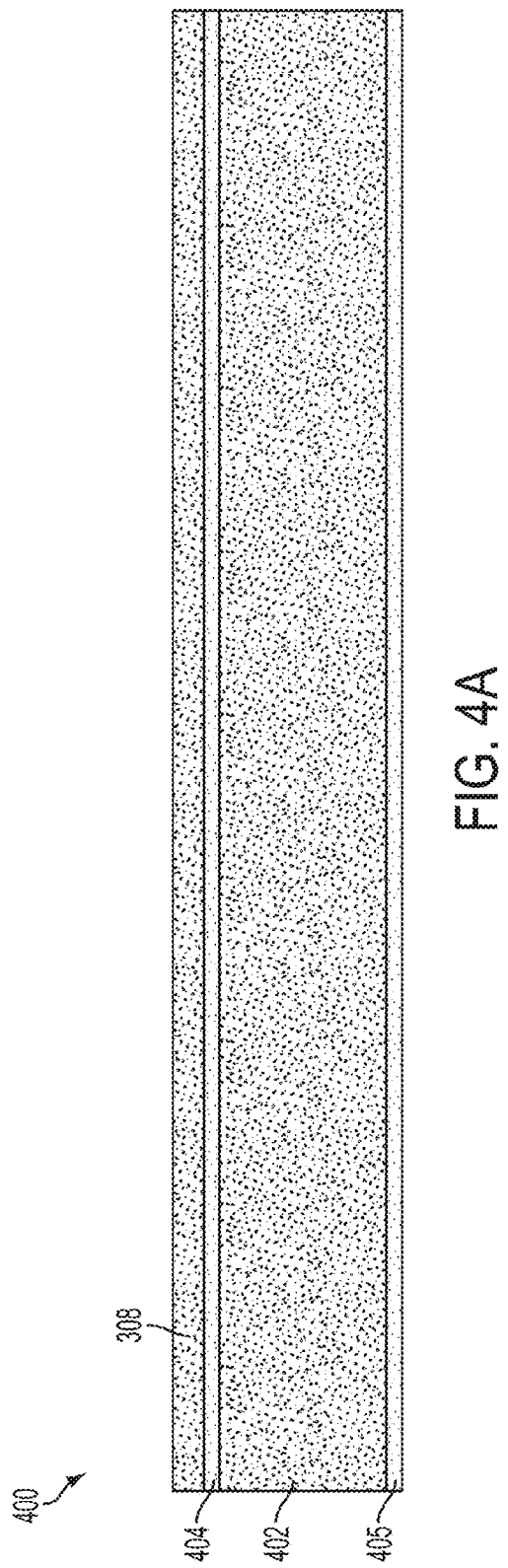
FIGS. 4A-4T illustrate a fabrication sequence, consistent with the fabrication sequence of FIG. 1, for forming the device of FIG. 3, according to a non-limiting embodiment of the present application.
Figure 4D:
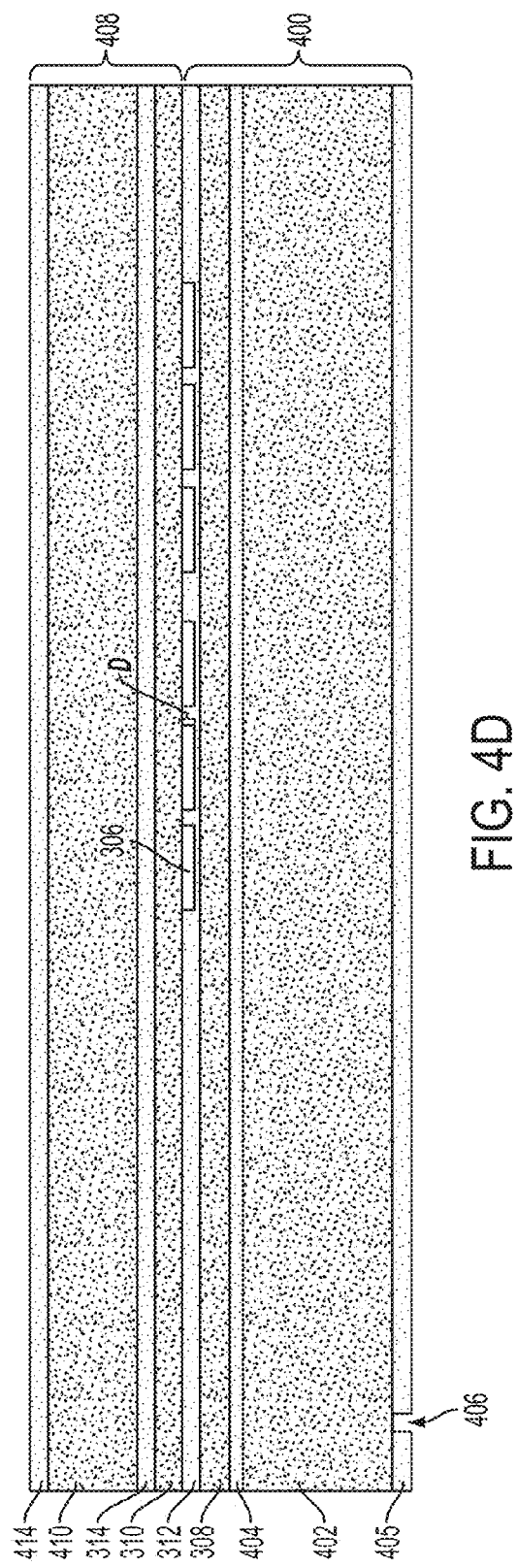
Figure 4E:
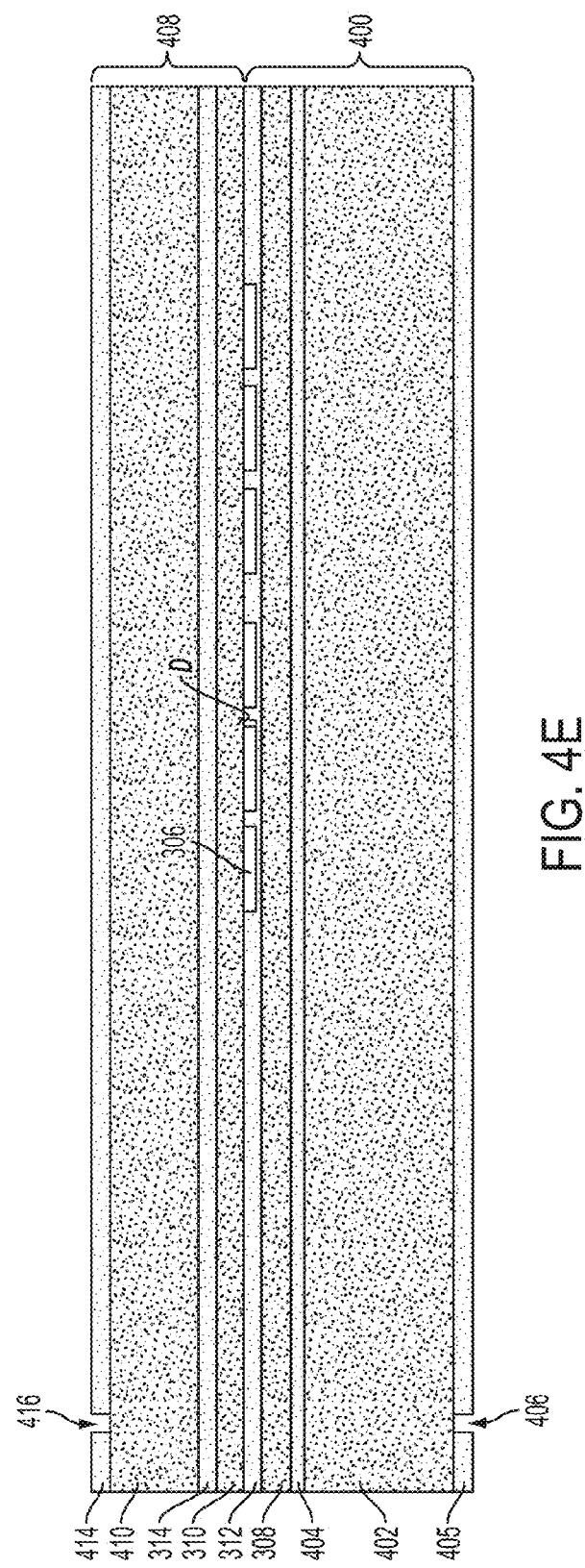
Figure 4L:
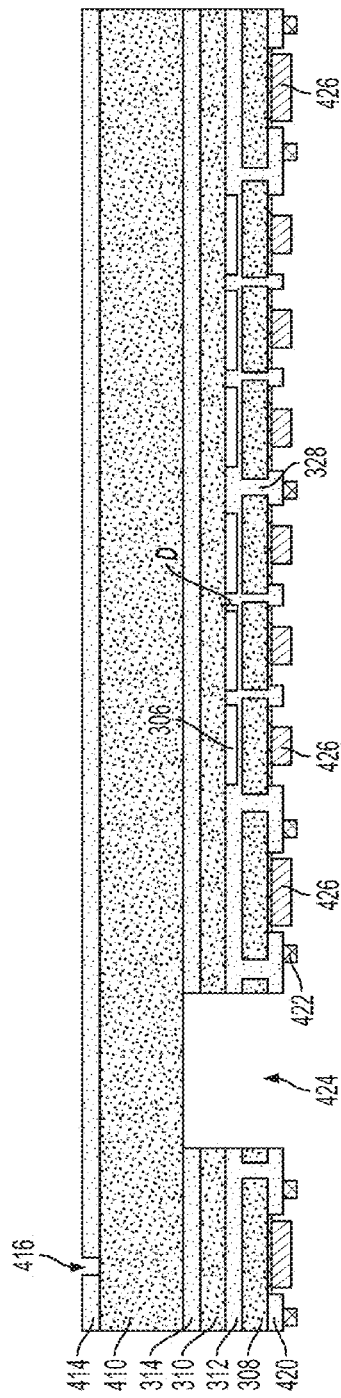
Figure 4M:
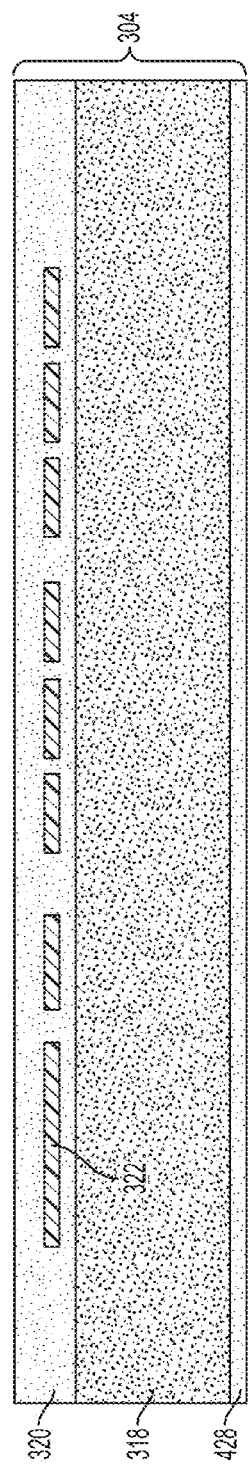
Figure 4P:
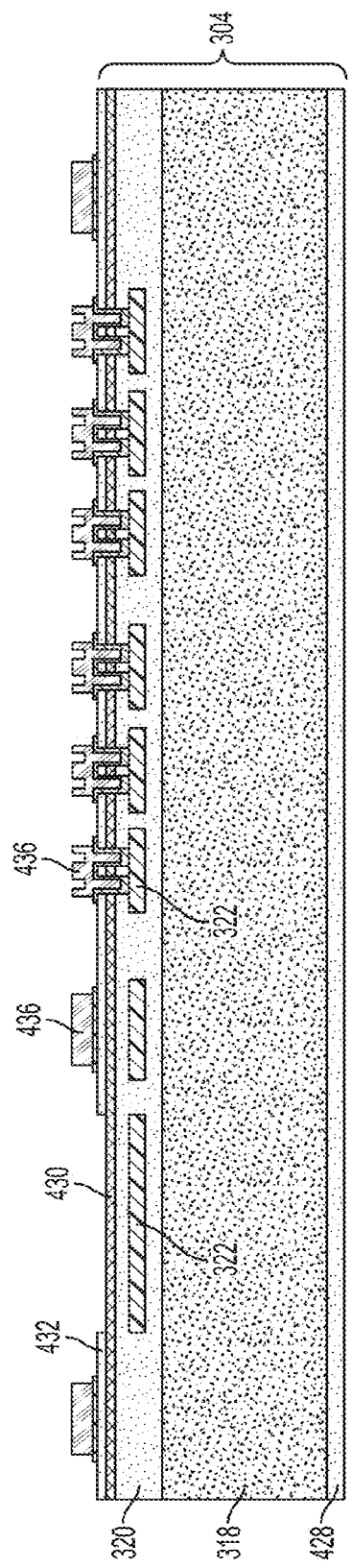
Figure 4Q:
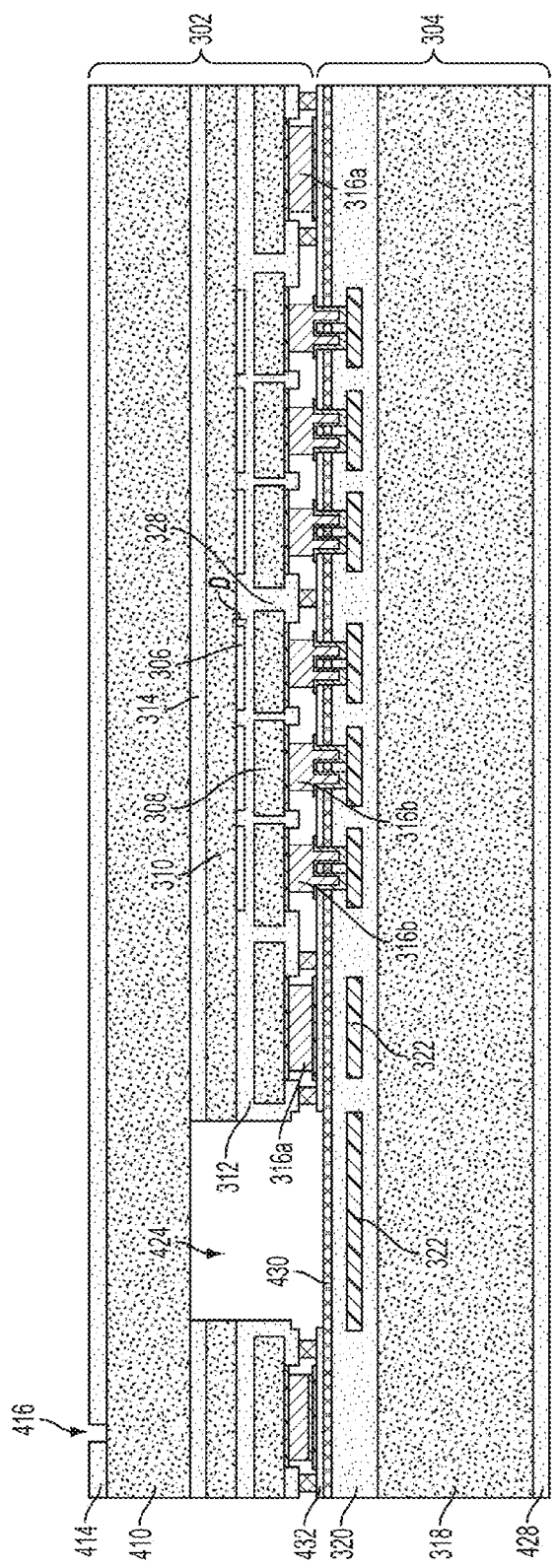
Figure 4R:
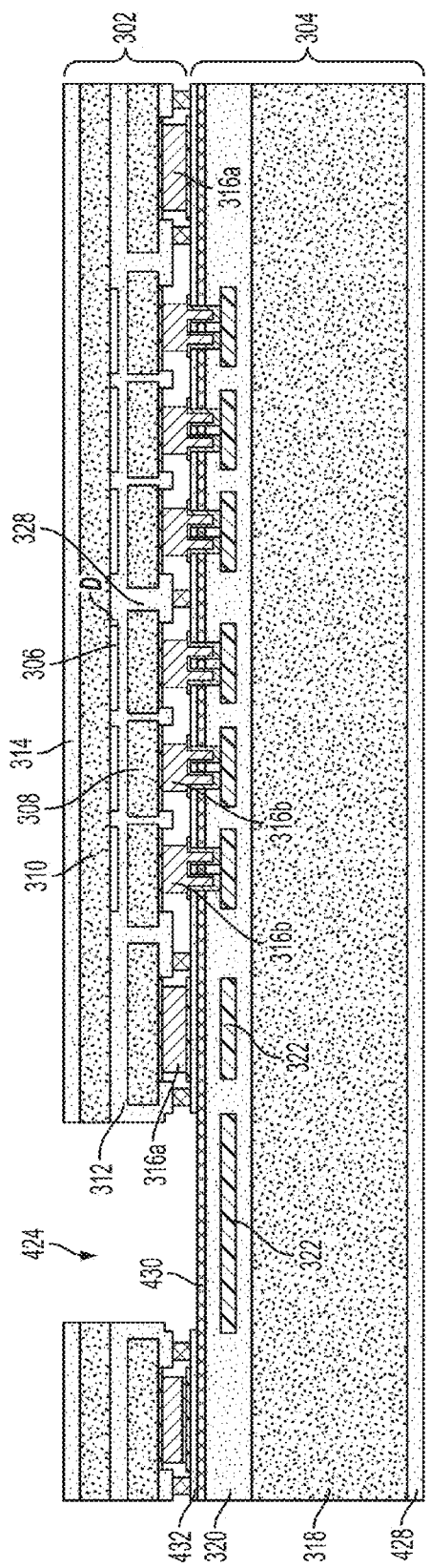
Figure 4T:
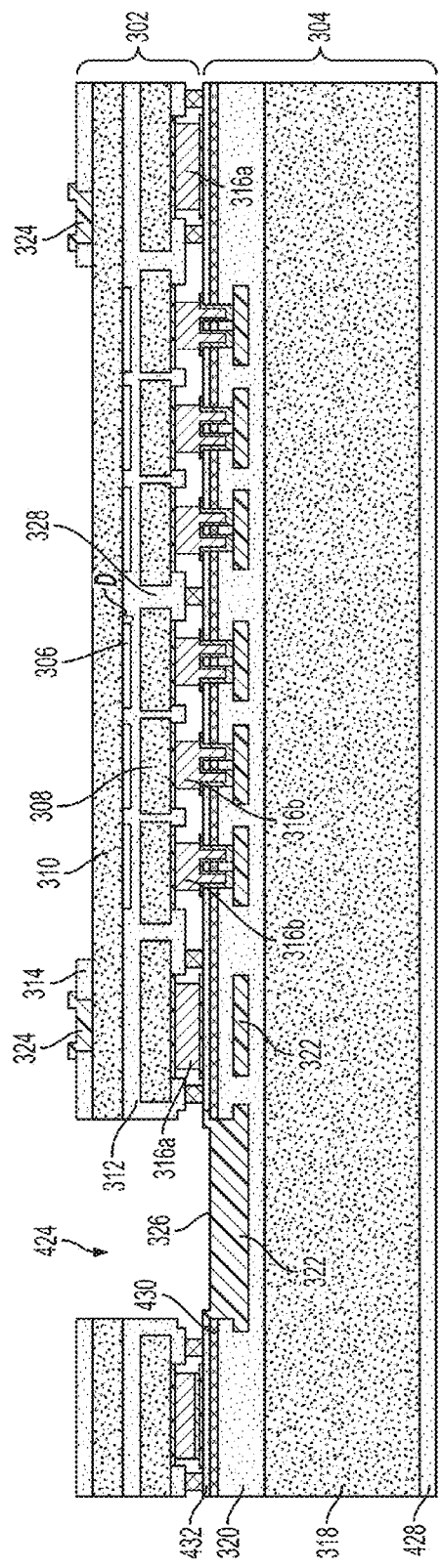

FIGS. 4A-4T illustrate a fabrication sequence for forming the device 300 of FIG. 3 consistent with the fabrication sequence of FIG. 1, according to a non-limiting embodiment of the present application. Structures previously described in connection with FIG. 3 retain the same reference numbers in FIGS. 4A-4T.

Initially, the formation of the engineered substrate is described, beginning as shown in FIG. 4A with a first SOI wafer 400. The SOI wafer 400 includes a handle layer 402 (e.g., a silicon handle layer), a BOX layer 404, and first silicon device layer 308. An oxide layer 405 may also be provided on the backside of the handle layer 402.

The first silicon device layer 308 may be formed of single crystal silicon and, as previously described, may be doped in some embodiments. As previously described in connection with FIG. 3, the first silicon device layer 308 may serve as a bottom electrode of an ultrasonic transducer, and thus suitable doping may provide desired electrical behavior. Also, using a doped silicon device layer avoids the need for using TSVs in some embodiments. In some embodiments, the first silicon device layer 308 may be highly doped P-type, although N-type doping may alternatively be used. When doping is used, the doping may be uniform or may be patterned (e.g., by implanting in patterned regions), for example to provide isolated electrodes as described further below in connection with FIG. 7. The first silicon device layer 308 may be doped already when the SOI wafer is procured, or may be doped by ion implantation, as the manner of doping is not limiting.

In some embodiments, the first silicon device layer 308 may be formed of polysilicon or amorphous silicon. In either case the first silicon device layer 308 may be doped or not as appropriate to provide desired electrical behavior.

As shown in FIG. 4B, the silicon oxide layer 312 may be formed on the SOI wafer 400. The silicon oxide layer 312 may be used to at least partially define the cavities 306 of the ultrasonic transducers, and thus may have any suitable thickness to provide for a desired cavity depth. Silicon oxide layer 312 may be a thermal silicon oxide, but it should be appreciated that oxides other than thermal oxide may alternatively be used.

FIG. 4B also illustrates that an alignment mark 406 may be formed (e.g., by suitable patterning of the oxide layer 405). As will be explained further below in connection with FIG. 4E, the alignment mark 406 may be later transferred to the second SOI wafer since the handle layer 402 will be removed.

As shown in FIG. 4C, the silicon oxide layer 312 may be patterned to form cavities 306, using any suitable technique (e.g., using a suitable etch). In this non-limiting embodiment, the cavities 306 do not extend to the surface of the first silicon device layer 308, although in alternative embodiments they may. In some embodiments, the silicon oxide layer 312 may be etched to the surface of the silicon device layer and then an additional layer of oxide (e.g., thermal silicon oxide) may be formed such that the cavities are defined by a layer of oxide. In some embodiments, the cavities may extend into the first silicon device layer 308. Also, in some embodiments structures such as isolation posts can be formed within the cavity.

Any suitable number and configuration of cavities 306 may be formed, as the aspects of the application are not limited in this respect. Thus, while only six cavities 306 are illustrated in the non-limiting cross-sectional view of FIG. 4C, it should be appreciated that many more may be formed in some embodiments. For example, an array of cavities 306 may include hundreds of cavities, thousands of cavities, or more to form an ultrasonic transducer array of a desired size.

The cavities 306 may have a depth D designed for desired operation of the ultrasonic transducers ultimately formed, for example in terms of frequency of operation. In some embodiments, the depth D may be approximately 2 microns, approximately 0.5 microns, approximately 0.25 microns, between approximately 0.05 microns and approximately 10 microns, between approximately 0.1 microns and approximately 5 microns, between approximately 0.5 microns and approximately 1.5 microns, any depth or range of depths in between, or any other suitable depth.

The cavities 306 may have a width W, also illustrated in FIG. 3. Non-limiting examples of values for W are described further below. The width dimension may also be used to identify the aperture size of the cavity, and thus the cavities 306 may have apertures of any of the values described herein for width W.

Figure 13:
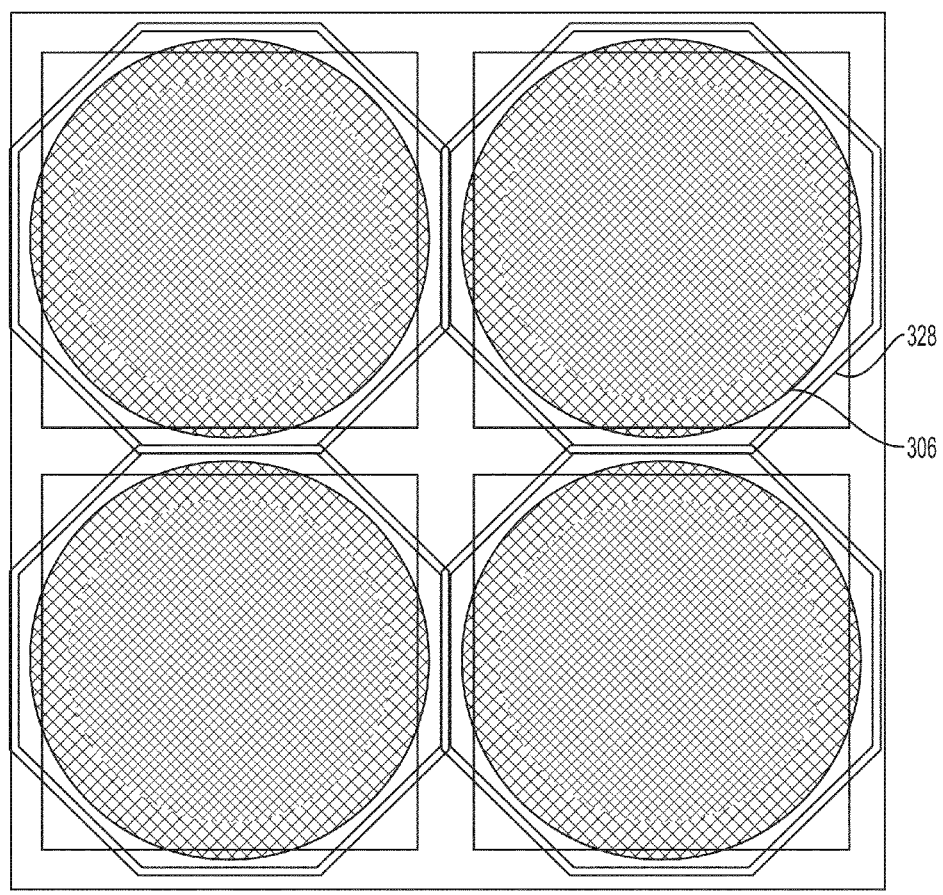
FIG. 13 is a top view illustrating an example of an isolation trench contour isolating ultrasonic transducers, according to a non-limiting embodiment.

The cavities 306 may take one of various shapes (viewed from a top side) to provide a desired membrane shape when the ultrasonic transducers are ultimately formed. For example, the cavities 306 may have a circular contour or a multi-sided contour (e.g., a rectangular contour, a hexagonal contour, an octagonal contour). An example of a circular contour is illustrated in FIG. 13, described below.

As shown in FIG. 4D, the first SOI wafer 400 may be bonded with a second SOI wafer 408 including a second handle layer (e.g., a silicon handle layer) 410, the oxide layer 314 (e.g., a BOX layer), and the second silicon device layer 310. The second SOI wafer 408 may additionally include an oxide layer 414. The bonding may be performed at a low temperature (e.g., a fusion bond below 450° C.), but may be followed by an anneal at a high temperature (e.g., at greater than 500° C.) to ensure sufficient bond strength. In those embodiments in which the first and/or second silicon device layers 308 and 310 are doped, the anneal may also serve to activate the doping, meaning that a single anneal may perform multiple functions. In the illustrated embodiment, the bond may be a Si—SiO$_2$ bond, although alternatives are possible. For example, in some embodiments the second SOI wafer 408 may include an oxide layer (e.g., a thermal silicon oxide) on the second silicon device layer 310, such that the bond between the first and second SOI wafers 400 and 408 may be a SiO$_2$—SiO$_2$ bond.

As with the first silicon device layer 308, the second silicon device layer 310 may be single crystal silicon, polysilicon, or amorphous silicon, and may be doped in some embodiments. The doping may avoid the need to form TSVs to provide electrical connectivity, and may be of any suitable type and level.

As shown in FIG. 4E, the alignment mark 406 may be transferred to the second SOI wafer as alignment mark 416.

Then, as shown in FIG. 4F, the oxide layer 405, handle layer 402, and BOX layer 404 may be removed, in any suitable manner. For example, grinding, etching, or any other suitable technique or combination of techniques may be used. As a result, the only layers remaining from the first SOI wafer 400 include the first silicon device layer 308 and the silicon oxide layer 312. As previously described in connection with FIG. 3, those layers may be thin. However, because they are bonded to the second SOI wafer 408 with its corresponding handle layer, sufficient structural integrity may be retained for further processing.

As previously described in reference to isolation structures 328 of FIG. 3, in some embodiments it may be desirable to electrically isolate one or more ultrasonic transducers of the device 300. Thus, as shown in FIG. 4G, one or more isolation trenches 418 may be formed in the first silicon device layer 308. In the illustrated embodiment, the isolation trenches 418 extend from a backside of the silicon device layer 308 to silicon oxide layer 312, and are narrower (in the direction of left to right in the figure) than the portion(s) of the overlying silicon oxide layer 312 to which each isolation trench 418 makes contact to prevent inadvertently punching through the silicon oxide layer 312 into the cavities 306. Thus, the isolation trenches 418 do not impact the structural integrity of the cavities 306. However, alternative configurations are possible.

FIG. 4H illustrates that the isolation trenches 418 may be filled with an insulating material 420 (e.g., silicon oxide) using any suitable technique (e.g., a suitable deposition). It should be noted that in the embodiment illustrated, the insulating material 420 completely fills the isolation trenches 418 and does not simply line the trenches 418, which may further contribute to the structural integrity of the device at this stage, rendering it more suitable for further processing.

In FIG. 4I, flow stop features 422 are optionally formed on the lower surface of the insulating material 420, for example using any suitable deposition and patterning technique. The flow stop features may perform one or more functions. For example, they may prevent undesirable flow of metal layers subsequently deposited. Alternatively or additionally, the flow stop features may provide a desired gap between the engineered substrate and CMOS wafer when later bonded. Thus, any suitable number and positioning of the flow stop features 422 may be provided to achieve one or both functions, and the flow stop features 422 may be formed of any suitable material. For example, the flow stop features 422 may be formed of silicon nitride (SiN) in some non-limiting embodiments. However, as described above, the use of flow stop features 422 is optional. For example, such features may be omitted in some embodiments, for example when using thermal compression for bonding the engineered substrate with another wafer.

As shown in FIG. 4J, the insulating material 420 may be patterned (using any suitable etch technique) in preparation for forming bonding locations for later bonding of the engineered substrate with a CMOS wafer. Also, the patterning may further define the isolation structures 328 described previously in connection with FIG. 3.

In FIG. 4K, a clear out region 424 may be formed through the first silicon device layer 308, the silicon oxide layer 312, the second silicon device layer 310, and the oxide layer 314. The clear out region 424 may isolate groups of ultrasonic transducers from each other (e.g., separating distinct ultrasonic transducer arrays), as will be described further below in connection with FIG. 6. For example, in some embodiments the first and second silicon device layers 308 and 310 are retained only in a region corresponding to an ultrasonic transducer array, with the clear out region 424 separating ultrasonic transducer arrays. The clear out region 424 may provide easier access to the CMOS wafer at a periphery of the ultrasonic transducer array, for example allowing for access to bond pads or other electrical connection features. The clear out region 424 may be formed in any suitable manner, for example using one or more of grinding, deep reactive ion etching (DRIE) and plasma etches for etching the silicon device layers and oxide layers. In some embodiments, grinding followed by DRIE is used. Alternative manners of forming the clear out region 424 are possible.

Bonding material 426 may then be formed on the engineered substrate in preparation for bonding the engineered substrate with a CMOS wafer, as shown in FIG. 4L. The type of bonding material 426 may depend on the type of bond to be formed. For example, the bonding material 426 may be a metal suitable for thermocompression bonding, eutectic bonding, or silicide bonding. In some embodiments, the bonding material may be conductive so that electrical signals may be communicated between the engineered substrate and the CMOS wafer as previously described in connection with FIG. 3 and bond points 316b. For example, in some embodiments the bonding material 426 may be gold and may be formed by electroplating. In some embodiments, materials and techniques used for wafer level packaging may be applied in the context of bonding the engineered substrate with the CMOS wafer. Thus, for example, stacks of metals selected to provide desirable adhesion, interdiffusion barrier functionality, and high bonding quality may be used, and the bonding material 426 may include such stacks of metals.

FIGS. 4M-4P relate to preparation of the CMOS wafer 304 for bonding with the engineered substrate. As shown in FIG. 4M, the CMOS wafer 304 includes the base layer (e.g., a bulk silicon wafer) 318, the insulating layer 320, and the metallization 322. An insulating layer 428 may optionally be formed on the backside of the base layer 318.

As shown in FIG. 4N, layers 430 and 432 may be formed on the CMOS wafer 304. The layer 430 may be, for example, a nitride layer and may be formed by plasma enhanced chemical vapor deposition (PECVD). The layer 432 may be an oxide layer, for example formed by PECVD of oxide.

In FIG. 4O, openings 434 may be formed from the layer 432 to the metallization 322. Such openings may be made in preparation for forming bonding points. For example, in FIG. 4P, bonding material 436 may be formed on the CMOS wafer 304 (by suitable deposition and patterning) at one or more suitable locations for bonding the engineered substrate 302 with the CMOS wafer 304. The bonding material 436 may be any suitable material for bonding with the bonding material 426 on the engineered substrate. As previously described, in some embodiments a low temperature eutectic bond may be formed, and in such embodiments the bonding material 426 and bonding material 436 may form a eutectic pair. For example, bonding material 426 and bonding material 436 may form an indium-tin (In—Sn) eutectic pair, a gold-tin (Au—Sn) eutectic pair, and aluminum-germanium (Al—Ge) eutectic pair, or a tin-silver-copper (Sn—Ag—Cu) combination. In the case of Sn—Ag—Cu, two of the materials may be formed on the engineered substrate as bonding material 426 with the remaining material formed as bonding material 436.

As shown in FIG. 4Q, the engineered substrate 302 and CMOS wafer 304 may then be bonded together, which in some embodiments results in a monolithically integrated structure including sealed cavities 306 disposed vertically above ICs in the CMOS wafer 304 (e.g., metallization 322). As previously described, such bonding may, in some embodiments, involve only the use of low temperature (e.g., below 450° C.) which may prevent damage to metallization layers and other components on the CMOS wafer 304.

In the non-limiting example illustrated, the bond may be a eutectic bond, such that the bonding material 426 and bonding material 436 may in combination form bond points 316a and 316b. As a further non-limiting example, a thermocompression bond may be formed using Au as the bonding material. For instance, the bonding material 426 may include a seed layer (formed by sputtering or otherwise) of Ti/TiW/Au with plated Au formed thereon, and the bonding material 436 may include a seed layer (formed by sputtering or otherwise) of TiW/Au with plated Ni/Au formed thereon. The layers of titanium may serve as adhesion layers. The TiW layers may serve as adhesion layers and diffusion barriers. The nickel may serve as a diffusion barrier. The Au may form the bond. Other bonding materials may alternatively be used.

Next, the second handle layer 410 and oxide layer 414 may be removed in any suitable manner as shown in FIG. 4R. For example, grinding and/or etching may be used. The oxide layer 314 may act as an etch stop for removing the second handle layer 410.

As shown in FIG. 4S, the oxide layer 314 may then be patterned to form openings 438 using any suitable etching technique. The openings 438 provide access to a backside (or topside) of the second silicon device layer 310 distal the CMOS wafer 304. As shown in FIG. 4T, the contacts 324 and bond pad 326 of FIG. 3 may then be formed, for example by depositing and patterning a suitable conductive material (e.g., aluminum, copper, or other suitable material). Also, the oxide layer 314 may optionally be removed (in any suitable manner) from regions overlying the cavities 306. That is, the oxide layer 314 may be removed from the ultrasonic transducer region of the ultrasound device.

The device 300 may then be achieved by depositing and patterning the passivation layer 330. As described previously in connection with FIG. 3, the passivation layer 330 may be patterned to provide access to one or more of the contacts 324.

Various features of the fabrication sequence of FIGS. 4A-4T are now noted. For example, it should be appreciated that the fabrication sequence does not involve the use of TSVs, thus making the process less costly and complex than if TSVs were used. The yield of the process may be increased as a result.

Additionally, the process does not utilize chemical mechanical polishing (CMP). For example, CMP is not used in preparation for either of the bonding stages described, and thus the bonding reliability (and therefore yield) may be increased while cost may be decreased compared to if CMP steps were performed. Similarly, it is noteworthy that the illustrated fabrication sequence does not include any densification anneals for the low temperature bond of the engineered substrate with the CMOS wafer. The use of such anneals reduces bonding reliability and therefore yield. Further still, and as previously described, the fabrication of the sealed cavities for the ultrasonic transducers is decoupled from the CMOS thermal budget, thus allowing for use of high temperature processing (e.g., a high temperature anneal) when bonding together the wafers of the engineered substrate.

The process for forming the sealed cavities 306 may also facilitate forming cavities of desired dimensions and spacing. For example, the cavities 306 may have widths W (see FIGS. 3 and 4C) of approximately 50 microns, between approximately 5 microns and approximately 500 microns, between approximately 20 microns and approximately 100 microns, any width or range of widths in between, or any other suitable widths. In some embodiments, the width W may be selected to maximize the void fraction, being the amount of area consumed by the cavities compared to the amount of area consumed by surrounding structures. The cavities 306 may have depths D (see FIG. 4C) of approximately 2 microns, approximately 0.5 microns, approximately 0.25 microns, between approximately 0.05 microns and approximately 10 microns, between approximately 0.1 microns and approximately 5 microns, between approximately 0.5 microns and approximately 1.5 microns, any depth or range of depths in between, or any other suitable depths. In some embodiments, the cavities have widths W of approximately 50 microns and depths D of approximately 0.2 microns. In some embodiments, a ratio of the width W to the depth D may be greater than 50, greater than 100, greater than 150, between 30 and 300, or any other suitable ratio. The ratio may be selected to provide desired operation of the transducer membrane, for example operation at a target frequency.

The spacing between cavities 306 may also be made small despite the fact that the amount of space between cavities 306 impacts the bondable area when forming the engineered substrate. That is, the smaller the distances are between the cavities 306 the less bonding surface is available which increases the difficulty of bonding. However, the processes of forming the engineered substrate described herein in connection with FIGS. 1, 2, 4A-4D, and 7 (described below), including cavity formation in an oxide layer, low temperature fusion bond, and high temperature anneal, make it practical to closely space the cavities 306 while still achieving high bond quality and yield of the engineered substrate. In general, because formation of the engineered substrate is not limited by a thermal budget using the techniques described herein, flexibility is provided in using design rules to minimize the bondable area between cavities 306. For example, spacing between cavities of less than 5 microns, less than 3 microns, or less than 2 microns, among other possibilities, may be achieved using the processes described herein.

Figure 5:
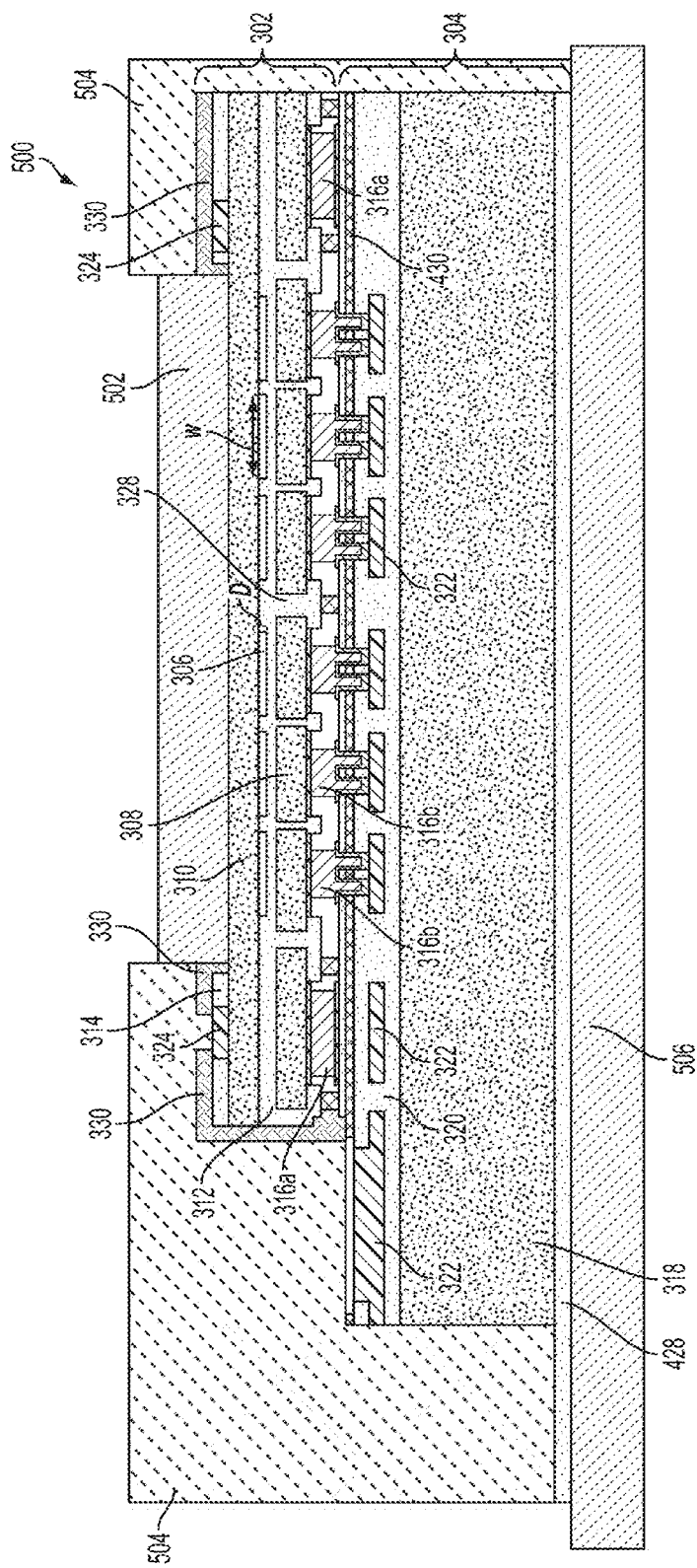
FIG. 5 is a cross-sectional view of the device of FIG. 3 with additional packaging.

The device 300 may be further packaged and/or encapsulated in some embodiments. For example, as shown by the packaged device 500 in FIG. 5, the device 300 may be diced and bonded with a substrate 506, which may be a circuit board, a plastic package backing (e.g., having contact pins in some embodiments), or other substrate. An acoustic medium 502 may be disposed over the ultrasonic transducer region of the device 300. The acoustic medium may be formed of silicone, parylene, or any other material providing desired acoustic properties. Further encapsulation may be provided by encapsulant 504. As previously described in connection with FIG. 3, in some embodiments wire bonds may be formed between contact 324 and bond pad 326, such as wire bond 325. The encapsulant 504 may be disposed to cover such wire bonds to protect them from damage (and thus the wire bond 325 is not shown in FIG. 5). Any suitable encapsulation material may be used for such a purpose. Thus, it should be appreciated the device 300 of FIG. 3 may be packaged, and the manner of packaging is not limiting of various aspects of the present application.

Figure 6:
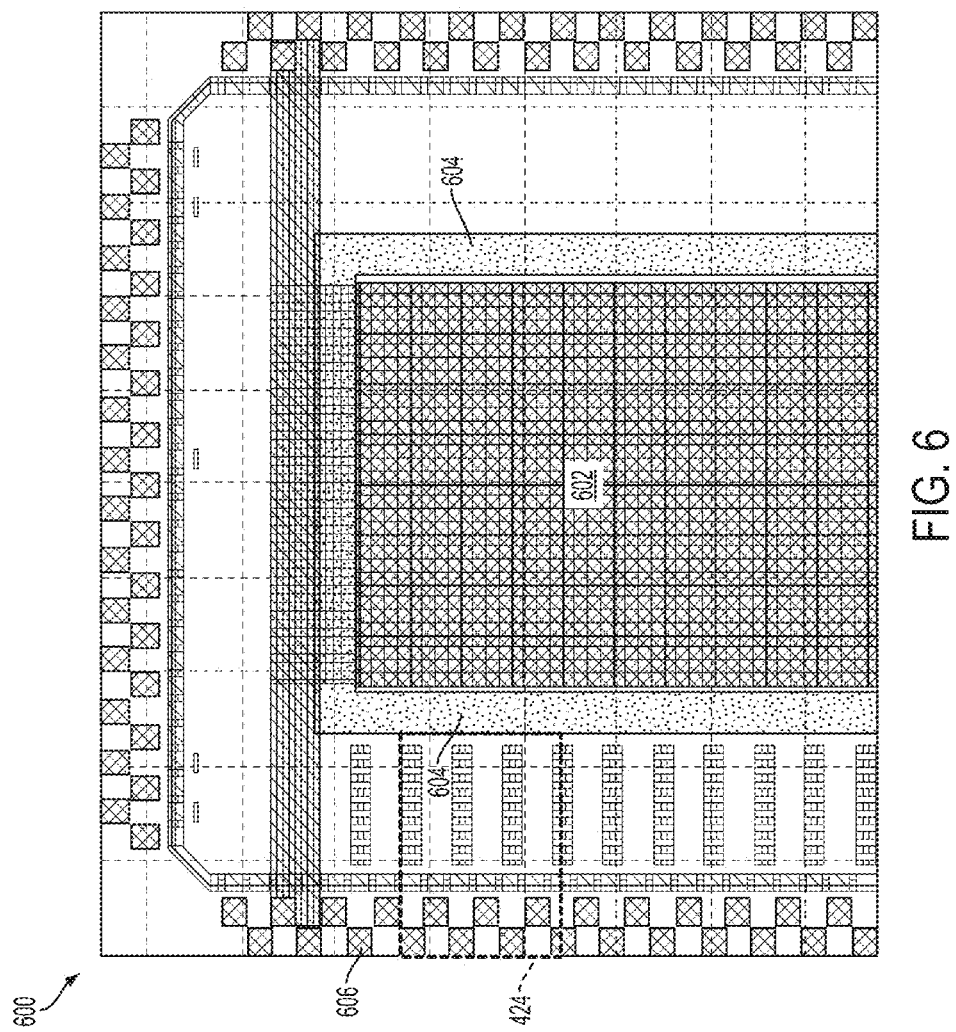
FIG. 6 is a top view of an ultrasound device including features of the device of FIG. 3, according to a non-limiting embodiment of the present application.

FIG. 6 illustrates a top view of a portion of an ultrasound device which may utilize the general structure of device 300. As shown, the ultrasound device 600 includes an array of ultrasonic transducers 602, which may correspond to the CMUTs previously described in connection with FIG. 3. A seal ring 604 may substantially or completely surround the ultrasonic transducers 602, although for simplicity only a portion of the seal ring 604 is illustrated. The seal ring may be formed by the bond points 316a previously described in connection with FIG. 3. In some embodiments, the seal ring 604 provides a hermetic seal, a hermetic seal being one which completely encloses an area via an unbroken contour. In some embodiments, the seal ring 604 provides electrical interconnection between an engineered substrate and features on a CMOS wafer (e.g., redistribution routing layers on a CMOS wafer, integrated circuitry on a CMOS wafer, or other features). In some embodiments the seal ring 604 provides a hermetic seal and electrical interconnection.

The clear out region 424, previously described in connection with FIG. 4K, may be provided around a periphery of the seal ring 604. As shown, the clear out region 424 may include various features, such as bond pads 606, which may correspond to bond pad 326 of FIG. 3.

Alternatives to the fabrication sequence of FIGS. 4A-4T are possible. For example, rather than using SOI wafers to form the engineered substrate 302, one or more bulk silicon wafers may be used. For example, the first SOI wafer 400 and/or second SOI wafer 408 may be substituted with a bulk silicon wafer. Referring to FIG. 4D, a reason for using SOI wafers 400 and 408 is that the BOX layers 404 and 314 may function as etch stops when the handle layers 402 and 410 are removed. Similar functionality may be achieved with a bulk silicon wafer using suitable doping to create a doped layer. That is, a portion of the bulk silicon wafer (e.g. corresponding to silicon device layer 308 or 310, and having any of the thicknesses described herein for such layers) may be doped to exhibit a lower etch rate than the majority of the bulk silicon wafer. Then, the bulk silicon wafer may be thinned (e.g., etched) from a backside until slowing or effectively stopping at the doped layer (that is, at the depth at which the doping changes the etch rate). In this manner, the doping gradient may effectively serve as an etch stop and thus a majority of the bulk wafer may be removed while leaving only a desired portion (e.g., the doped layer corresponding to silicon device layer 308 or 310). Alternatively, bulk silicon wafers may be used and thinned to a desired thickness using a timed etch. The remainder of the fabrication sequence of FIGS. 4A-4T may proceed in substantially the same manner described with respect to the use of SOI wafers, and thus may similarly be used to produce the device 300 of FIG. 3. One advantage to using bulk silicon wafers in this manner is their relatively low cost compared with SOI wafers.

Figure 7:
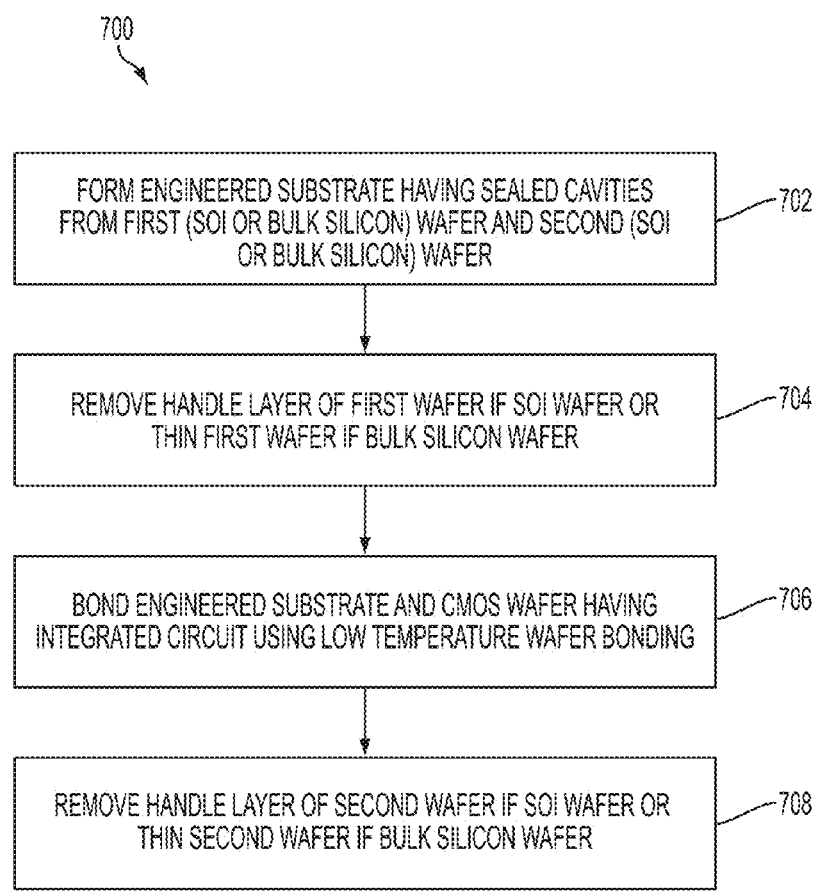
FIG. 7 is a flowchart of a fabrication sequence for fabricating an ultrasonic transducer integrated with a CMOS wafer, and encompasses the method of FIG. 1, according to a non-limiting embodiment of the present application.

From the foregoing, it should be appreciated that the method of FIG. 1 may be generalized without limitation specifically to SOI wafers, as is done in FIG. 7. As shown, the method 700 may begin at stage 702 with the formation of an engineered substrate having sealed cavities from a first wafer, which may be an SOI wafer or a bulk silicon wafer, and a second wafer, which also may be an SOI wafer or a bulk silicon wafer. Thus, it should be appreciated that stage 702 of method 700 may involve use of two SOI wafers, as in FIG. 1, two bulk silicon wafers, or one SOI wafer and one bulk silicon wafer.

One or both of the two wafers used in stage 702 may have a plurality of cavities formed therein, such that bonding the two wafers together may result in sealed cavities suitable for use as the cavities of CMUTs. To ensure a strong bond between the two wafers, high temperature processing may be used. For example, a high temperature anneal may be used subsequent to a low temperature wafer bond, such as a low temperature fusion bond. Thus, a combination of high and low temperatures may be used in forming the engineered substrate in some embodiments. As described in connection with FIG. 1, high temperature may, in some embodiments, be above 450° C., a temperature threshold above which CMOS ICs would typically be damaged. Also, just as with the bonding at stage 102, the bonding of the two wafers at stage 702 may be performed in vacuum.

At stage 704, the thickness of the first wafer is altered. If the first wafer is an SOI wafer, then a handle layer of a first wafer is removed. If the first wafer is instead a bulk silicon wafer, then it may be thinned, for example by etching. A timed etch may be used or the bulk silicon wafer may include a doping gradation functioning as an etch stop, as described previously herein.

As a result of stage 704, the first wafer may have a relatively small thickness. For example, the thickness of the first wafer after stage 704 may be less than 50 microns, less than 30 microns, less than 20 microns, or less than 10 microns. As will be described further below, the first wafer will, in some embodiments, subsequently be bonded with a CMOS wafer such that it is disposed between the CMOS wafer and the second wafer. A gap may exist between the first wafer and the CMOS wafer in the manner described previously with respect to the gap between CMOS wafer 304 and first silicon device layer 308 of FIG. 3. Applicants have appreciated that this gap may allow for the first wafer to vibrate if the first wafer is too thin. Such vibration may be undesirable, for instance since it can generate unwanted harmonics from the ultrasonic transducer. Thus, Applicants have recognized that the first wafer should preferably have a sufficient thickness to provide rigidity avoiding such undesirable vibration. Thus, according to an embodiment, stage 704 is performed such that the thickness of the first wafer is between 4 microns and 50 microns, between 5 microns and 30 microns, between 6.5 microns and 20 microns, between 8 microns and 15 microns, or assumes any thickness or range of thicknesses within such ranges. Although the first wafer may therefore be thin, Applicants have appreciated that the second wafer at this stage of method 700 may provide sufficient structural support to allow for further processing of the engineered substrate.

At stage 706, the engineered substrate may be bonded with a CMOS wafer having integrated circuitry to form an integrated device, in the same manner described in connection with stage 106 of FIG. 1. The first wafer may be arranged proximate the bonding surface of the CMOS wafer, for example by bonding a backside of the first wafer with the CMOS wafer. Thus, the resulting structure may include, in order, a CMOS wafer, the first wafer, and the second wafer. As previously described, depending on the type of bonding performed, a gap may exist between the CMOS wafer and the first wafer, for example as described in connection the first silicon device layer 308 and the CMOS wafer 304 of FIG. 3.

At stage 708, the thickness of the second wafer is altered. If the second wafer is an SOI wafer, then the handle layer of the second wafer of the engineered substrate is removed, in any suitable manner, for example by a combination of grinding followed by etching. If the second wafer is instead a bulk silicon wafer, then it may be thinned, for example by etching. A timed etch may be used or the bulk silicon wafer may include a doping gradation functioning as an etch stop.

As with the method 100 of FIG. 1, the method 700 results, in some embodiments, in an engineered substrate integrated with a CMOS wafer, where the engineered substrate includes only two silicon layers. Such a structure has the benefits described previously in connection with FIG. 1.

Electrical connections may be made between the ICs on the CMOS wafer and the sealed cavities of the engineered substrate to provide functioning ultrasonic transducers in the same manner described in connection with FIG. 1.

In accordance with the method 700, an alternative to the fabrication sequence of FIGS. 4A-4T is an embodiment in which one SOI wafer and one bulk silicon wafer are used to form the engineered substrate. Referring to FIG. 4A, the SOI wafer 400 is replaced with a bulk silicon wafer having oxide on its front and rear surfaces. That is, the structure of FIG. 4B minus the BOX layer 404 may be used. Then, cavities may be formed in the silicon oxide layer on the front face of the bulk silicon wafer, in the same manner as shown in FIG. 4C. That is, the current embodiment may differ from what is shown in FIG. 4C only in that the BOX layer 404 may be absent, since a bulk silicon wafer is used in this embodiment.

The bulk silicon wafer with cavities may then be bonded with an SOI wafer, such as SOI wafer 408. Thus, the present embodiment may differ from the structure of FIG. 4D only in that the BOX layer 404 may be absent.

Thereafter, processing in the present embodiment may proceed in the same manner as illustrated in FIGS. 4E-4T.

Yet another alternative to the fabrication sequence of FIGS. 4A-4T, and consistent with the method 700, is illustrated in connection with FIGS. 8A-8D. Here, fabrication begins as shown in FIG. 8A with the SOI wafer 400 of FIG. 4A. The next stage, shown in FIG. 8B, is the same as that of FIG. 4B.

Next, as shown in FIG. 8C, cavities 806 are formed in the silicon oxide layer 312. The cavities 806 extend through the silicon oxide layer 312, stopping on the first silicon device layer 308. Such a configuration may be achieved by etching the silicon oxide layer 312 with an etch for which the first silicon device layer 308 serves as an etch stop. Using the first silicon device layer 308 as an etch stop facilitates accurate control of the depth of the cavities 806.

Next, as shown in FIG. 8D, the SOI wafer 400 (with cavities 806 extending through the silicon oxide layer 312) is bonded with a bulk silicon wafer 808. The bulk silicon wafer 808 includes a silicon layer 810, the oxide layer 314 on a front surface of the silicon layer 810, and the oxide layer 414 on a rear surface (or backside) of the silicon layer 810. Thus, at this stage of fabrication the cavities 806 may be sealed.

Thereafter, fabrication may proceed in substantially the same manner as shown with respect to FIGS. 4E-4T. That is, subsequent to the stage illustrated in FIG. 8D, the alignment mark may be transferred to the bulk silicon wafer. The bulk silicon wafer 808 may then be thinned from the backside (from the side on which oxide layer 414 is disposed) to achieve a structure similar to that of FIG. 4F. From this stage on, the thinned bulk silicon wafer may be processed in the same manner as is the first silicon device layer 308 in FIGS. 4G-4T.

Various parameters associated with the device may be selected to optimize performance of the device. Examples of such parameters include the depth D of the cavities (determined by the thickness of silicon oxide layer 312 in the non-limiting embodiment of FIG. 8D), the thickness of oxide layer 314, the width W of the cavities, the pitch of the cavities, and the thickness of the resulting membrane. For example, the depth D of the cavities and the thickness of oxide layer 314 may be selected to optimize transmit and receive functionality of the ultrasonic transducer in imaging modes, and also to allow for low voltage operation. The membrane thickness, cavity width and pitch may be selected to facilitate low frequency operation in high intensity focused ultrasound (HIFU) modes, and may be used to control the sensitivity and bandwidth of the ultrasonic transducer, as an example.

Another alternative to the fabrication sequence of FIGS. 4A-4T relates to isolation of the bottom electrodes corresponding to the sealed cavities 306. As shown in FIG. 3, isolation structures 328 may be provided and, as illustrated in connection with FIGS. 4G-4J, in some embodiments the isolation structures 328 are trenches filled with insulating material. However, alternative isolation structures may be used, one of which includes isolated regions formed by doping of the first silicon device layer 308. That is, rather than forming trenches (e.g., trenches 418 in FIG. 4G) at each location at which isolation is desired, doping boundaries may be used instead, for example to define one or more reverse biased diodes. An example is illustrated in FIG. 9.

The device 900 of FIG. 9 represents an implementation of the device 300 of FIG. 3 in which doping boundaries are used to create the isolation structures 328. In FIG. 9, the first silicon device layer 308 is shown as having three different types of regions representing differences in doping. The regions 902 represent the base doping of the silicon material. The regions 904 represent electrode regions and are oppositely doped from the regions 902. The regions 906, which are optional, represent regions having the same dopant type as the electrode regions 904, but having a lower doping concentration. As a result of the opposite doping of the regions 902 and 904, isolation between electrode regions 904 may be created by using a suitable doping pattern as shown to create p-n junctions between the electrode regions 904. The p-n junctions may be reverse biased in some embodiments.

One suitable doping scheme is for regions 902 to be lightly doped N-type, regions 904 to be heavily doped P-type, and regions 906 to be lightly doped P-type. However, in an alternative embodiment regions 902 may be lightly doped P-type, regions 904 may be heavily doped N-type, and regions 906 may be lightly doped N-type. Under either scenario, boron may serve as the P-type dopant and phosphorous or arsenic may serve as the N-type dopant, although are alternatives are possible. The doping concentrations of the regions 902, 904, and 906 may be selected to provide desired electrical behavior.

The doping of regions 902, 904, and 906 may be created in any suitable manner. According to some embodiments, a combination of ion implantation and diffusion (e.g., via high temperature anneal) may be used. As shown in FIG. 9, the regions 904 and 906 may extend through the entire thickness of first silicon device layer 308, the thickness of which has been previously described. To extend the doping regions 904 and 906 through such thicknesses, ion implants of, for example, 750 keV, 1 MeV, between 500 keV and 2 MeV, or up to 10 MeV may be coupled with diffusing anneals, a combination which may be iterated in some embodiments until the doping regions 904 and/or 906 extend through the first silicon device layer 308. However, because such high energy implants may penetrate deeply into the first silicon device layer 308, lower energy implants may additionally be used to ensure that shallower depths of the first silicon device layer 308 are also doped. The energy of the implant(s) and the anneal duration and temperature may depend on the type of dopant being used, since some dopants may reach greater depths more readily than others (e.g., boron may implant further than phosphorous for the same given implant energy).

The sizing of the regions 902, 904, and 906 may be selected to provide desired electrical behavior. For example, the sizing may be optimized to reduce parasitic capacitance, for example between distinct electrode regions 904. Since regions 904 represent electrode regions corresponding to the cavities 306, they may be sized to provide a desired electrode size. For example, the regions 904 may have widths substantially equal to the width W of the cavities 306, although in alternative embodiments regions 904 may have a smaller width than the width W of the cavities (see FIG. 3), which may be beneficial to reduce dead (parasitic) capacitance.

As previously described, the regions 906 are optional and thus may be omitted in some embodiments. The regions 906 may reduce dead capacitance between the electrode regions 904, and thus when included may have any suitable sizing to perform such a function. For example, in some embodiments the regions 904 may be relatively large compared with the widths of the electrode regions 904. Thus, the locations of regions 904 and 906 may be controlled to provide desired sizing and spacing relative to the cavities 306.

The regions 902 may be electrically connected to any suitable voltage. In some embodiments, the regions 902 may be floating. In other embodiments, the regions 902 may be tied to a bias voltage. For example, regions 902 may be electrically grounded when doped P-type, or may be tied to a high voltage (e.g., a high voltage rail) when doped N-type. In some embodiments, the regions 902 may be tied to a voltage between approximately 20-300 Volts (e.g., between approximately 30-120 Volts, between approximately 50-250 Volts, between approximately 60-90 Volts, or any value or any range of values within these ranges) as may be used in the context of ultrasound imaging applications, as a non-limiting example. In some embodiments, the regions 902 may be biased at the same (or substantially the same) voltage as used to bias the second silicon device layer 310 serving as a membrane for the ultrasonic transducers.

While FIG. 9 illustrates patterned doping of the first silicon device layer 308, it should be appreciated that patterned doping may also be used with the second silicon device layer 310 in the same manner as described with respect to first silicon device layer 308. Thus, interconnected and doped ultrasonic transducer membranes may be formed in the second silicon device layer 310. For example, multiple distinct regions of higher doping of the second silicon device layer 310 may be alternated with regions of lower doping of the same doping species. Other patterns are also possible.

In those embodiments in which both the first and second silicon device layers 308 and 310 are doped, the relative doping between the two layers may be selected to provide desirable electrical behavior. For example, regions 904 and the second silicon device layer 310 may be oppositely doped and doped to different concentrations to amplify a bias voltage. For example, the regions 904 may be doped P+ and the second silicon device layer 310 may be doped N−. Such a configuration may produce an extra voltage drop across the cavities 306 (e.g., on the order of 1 Volt) arising from the different work functions of the N and P doping. If the regions 904 are doped N-type, it may be advantageous to also dope the second silicon device layer 310 N-type to avoid losing a voltage drop due to the work functions.

A further alternative to the fabrication sequence of FIGS. 4A-4T relates to the item to which the engineered substrate is bonded. As has been described, for example with respect to device 300, the engineered substrate is bonded with a CMOS wafer in some embodiments. In some embodiments, the CMOS wafer includes integrated circuitry. In some embodiments, the CMOS wafer includes integrated circuitry and redistribution layers processed thereon. In some embodiments, the CMOS wafer may only include redistribution layers processed thereon. Further alternatives are possible. For example, the engineered substrate may alternatively be bonded with an interposer, a device electrically (and sometimes physically) configured intermediate two devices and having interconnects configured to electrically couple together the two devices (e.g., the engineered substrate and another device, such as a ball grid array or other device). In some embodiments, the engineered substrate may be bonded with a wafer that does not include integrated circuitry, but rather which may include wiring for communicating electrical signals with the first and/or second silicon device layer. For example, in some embodiments the engineered substrate may be bonded with a wafer which includes wiring traces configured to redistribute electrical signals to a smaller or larger substrate, and which thus may be referred to herein as a "redistribution wafer".

A further alternative relates to the manner of making electrical contact to the second silicon device layer 310. As described previously, in the embodiment of FIG. 3, electrical contact may be made between the contact 324 and the bond pad 326, for example using a wire bond 325. As shown in FIG. 10, a device 1000 of an alternative construction utilizes a via 1002 from the bond point 316a to the second silicon device layer 310. In this manner, an embedded contact may be used and wire bonds may be avoided. Suitable insulating features (e.g., an insulating liner) may be used in some embodiments to insulate the via 1002 from the first silicon device layer 308 when it is desired for the first and second silicon device layers to be electrically isolated. However, as described previously, in some embodiments it may be desirable to electrically tie a region of the first silicon device layer 308 (e.g., the regions 902 of FIG. 9, when included) to the same potential as the second silicon device layer 310, and in such embodiments no insulating feature may be provided with the via 1002.

It should be appreciated that the via 1002 is not a traditional TSV because the thickness through which it passes, namely the thickness of the second silicon device layer 310, the silicon oxide layer 312, and the first silicon device layer 308 may be relatively small, for example having any of the dimensions previously described herein with respect to such structures.

Figure 11:
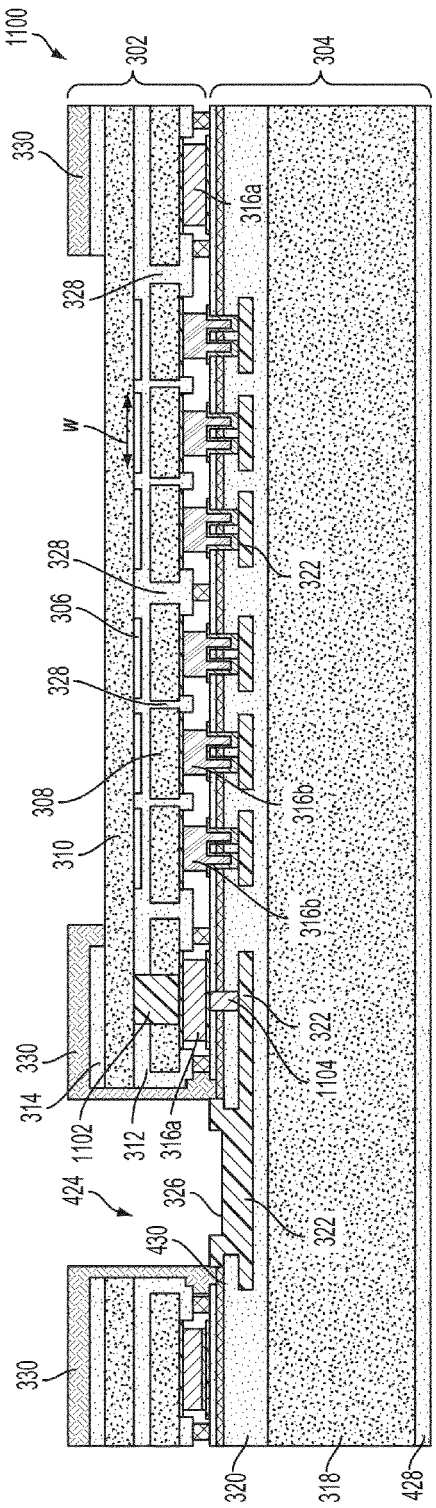
FIG. 11 illustrates a variation on the device 300 of FIG. 3 and an alternative to the device of FIG. 10, in which an embedded contact provides electrical connection to an ultrasonic transducer membrane, according to a non-limiting embodiment of the present application.

As a further alternative, the via 1002 representing an embedded contact may not pass through the second silicon device layer 310, but rather may extend between the bond point 316a and the bottom side of the second silicon device layer 310 proximate the cavity 306, while again being insulated from the first silicon device layer 308 by a suitable insulating feature (e.g., an insulating liner). An example is illustrated in FIG. 11, in which device 1100 includes embedded via 1102 which extends from the bond point 316a to the surface of second silicon device layer 310, but which does not pass through the second silicon device layer 310. An additional interconnection 1104 may be provided from the metallization 322 to the bond point 316a and the metallization 322 may be connected to the bond pad 326 as shown, forming a continuous electrical path from the bond pad 326 to the via 1102. However, other configurations for providing electrical access to the via 1102 are also possible.

In a configuration like that in FIG. 11, the via (e.g., via 1102) may be, for example, fabricated through the first silicon device layer 308 and silicon oxide layer 312 (e.g., after the stage of processing illustrated by FIG. 4J) prior to bonding the engineered substrate with the CMOS wafer, and the act of bonding the engineered substrate with the CMOS wafer may complete the electrical connection from the bond point 316a to the second silicon device layer 310. Such a configuration may eliminate the need for any metal on the topside of the second silicon device layer 310 as shown in FIG. 11, which may simplify fabrication and improve performance of the ultrasonic transducer membrane formed by the second silicon device layer 310.

A further alternative to the device 300 combines features of the devices of FIGS. 10 and 11. The via 1002 of FIG. 10 may be included and may connect to metallization on the topside of the second silicon device layer 310. The interconnection 1104 of FIG. 11 may be included as well. In such embodiments, an electrical path may be provided from the metallization 322 to metallization on the topside of second silicon device 310 without the need for a wire bond.

Figure 12:
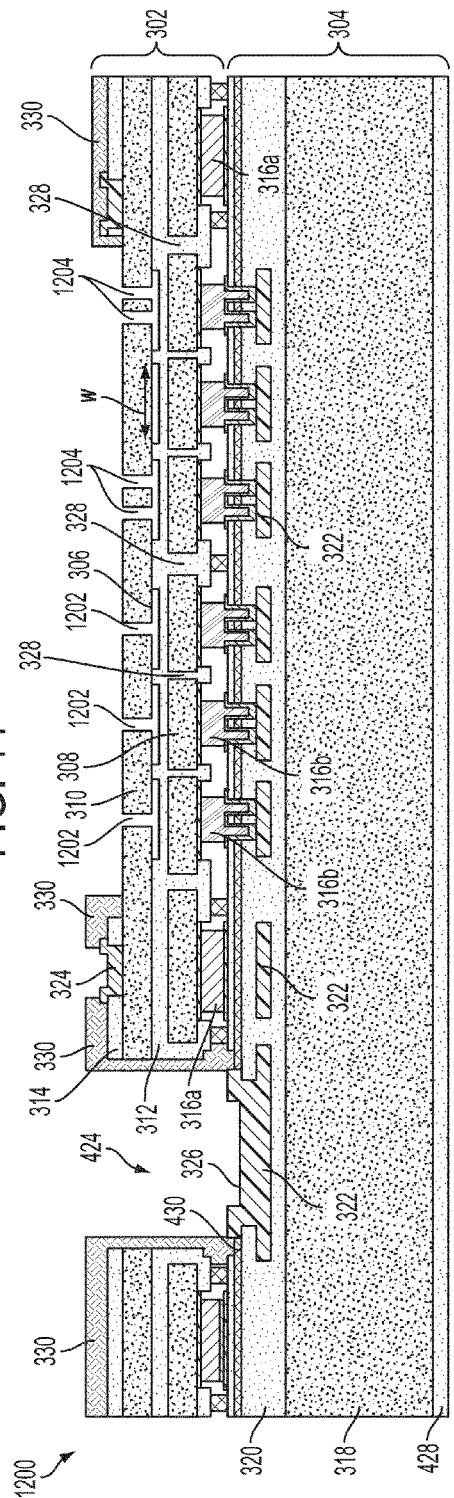
FIG. 12 illustrates a variation on the device 300 of FIG. 3 in which the cavities of the ultrasonic transducers are not sealed, according to a non-limiting embodiment.

A further alternative to the device 300 and fabrication sequence of FIGS. 4A-4T relates to whether the cavities 306 are sealed. As has been described previously, in some embodiments the cavities 306 may be sealed cavities. However, in alternative embodiments the cavities 306 may not be sealed, for example there being one or more openings to the cavities. An example is shown in FIG. 12.

The device 1200 is similar to the device 300 of FIG. 3 but differs in that openings are provided to the cavities 306 through the second silicon device layer 310. Two different non-limiting examples of openings are illustrated. In some embodiments, a single opening 1202 may be provided for each of one or more (but not necessarily all) cavities 306. In some embodiments, multiple openings 1204 may be provided for each of the one or more (but not necessarily all) cavities. Although two different patterns of openings are shown in FIG. 12 for purposes of explanation, it should be appreciated that a single pattern (e.g., just openings 1202 or just openings 1204) may be used for the entire device 1200. Also, while the openings 1202 and 1204 are shown as extending vertically through the second silicon device layer 310, it should be appreciated that other paths and geometries of openings may be used. For example, trenches formed along the side of the device may be used to access the cavities 306.

The openings 1202 and/or 1204 may be formed in any suitable manner and at any suitable stage of processing of the device 300. For example, the openings 1202 and/or 1204 may be formed after the fabrication stage illustrated in FIG. 4T using a suitable etch.

The presence of openings 1202 and/or 1204 may impact the loss and stiffening of the ultrasonic transducers, and ultimately the frequency of operation. For example, the openings 1202 and/or 1204 will result in the device acting more as a broadband device than if the openings were not included, and result in improved ranging behavior. The size of the openings 1202 and/or 1204 impacts the frequency characteristics, and in some embodiments may be selected to match a Helmholtz resonance frequency for the device 1200.

Thus, openings 1202 and/or 1204 may be beneficial to providing desired ultrasonic transducer frequency characteristics. For example, openings 1202 and/or 1204 may facilitate achieving desired frequency behavior for the ultrasonic transducers in open-air applications (lacking a transducing medium).

FIG. 13 illustrates a top view of an example of the shape of the isolation structures 328 isolating the sealed cavities 306. As shown, in one embodiment the sealed cavities 306 may have a circular contour. The isolation structures 328 may have any suitable shape to provide sufficient isolation between ultrasonic transducer elements or, as shown in FIG. 13, between individual ultrasonic transducers. Thus, in some embodiments the isolation structures 328 may substantially or completely surround (or encircle) the sealed cavities 306 (when viewed from a topside), although in alternative embodiments they may not surround the sealed cavities. Also, in some embodiments the isolation structures may have a contour within the sealed cavity (when viewed from a topside). For instance, when doping regions are used to define the isolation structures as described in connection with FIG. 9, the doping regions may be positioned to define a contour of the isolation structure that is smaller than a contour of the sealed cavity.

In some embodiments, the isolation structures 328 may have a multi-sided contour. For example, an octagonal contour is shown in FIG. 13, although it should be appreciated that other contours are possible (e.g., circular, rectangular, hexagonal, a contour defining more than a semi-circle, etc.). Also, as previously described, in some embodiments the isolation structures may surround multiple cavities 306 rather than individually surrounding each cavity. Thus, various configurations for the isolation structures are possible.

A further alternative to the device 300 and fabrication sequence of FIGS. 4A-4T relates to the use of TSVs. As has been described previously, many embodiments described herein avoid the need for TSVs, which can provide significant benefits in terms of, for example, ease of manufacturing, low cost, and reliability. Nonetheless, in some embodiments TSVs may be used. An example is described in connection with FIG. 14.

Figure 14:
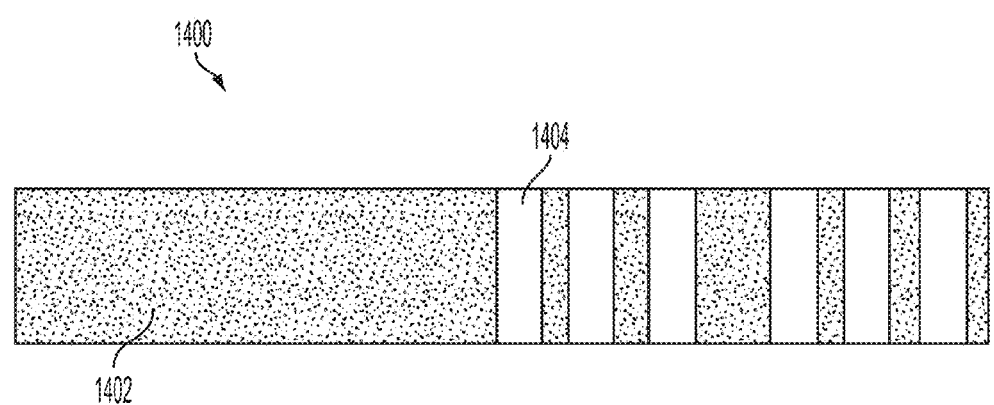
FIG. 14 illustrates a silicon wafer with TSVs, as may be used to fabricate an engineered substrate according to a non-limiting embodiment of the present application.

In some embodiments, a wafer having TSVs may be used in forming an engineered substrate. FIG. 14 illustrates a wafer 1400 including silicon 1402 and TSVs 1404, of which there are six. The wafer 1400 may be used, for example, in place of an SOI wafer in the fabrication sequence of FIGS. 4A-4T. As an example, the wafer 1400 may be used in place of first SOI wafer 400. In such a scenario, then, the structure of FIG. 4F may differ in that the first silicon device layer 308 would be replaced by silicon 1402 and the TSVs 1404 would align with cavities 306. Thus, the TSVs 1404 may function as electrodes, and accordingly may be used, for example, as an alternative to the doping scheme of FIG. 9 to form electrodes.

An embodiment involving use of a wafer with TSVs, as just described in connection with FIG. 14, may simplify fabrication of bottom electrodes for the sealed cavities of an engineered substrate, since the TSVs may function as the electrodes. The cavities may be aligned with the TSVs through suitable design.

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Aspects of the present application provide manufacturing processes suitable for formation of monolithically integrated ultrasonic transducers and CMOS structures (e.g., CMOS ICs). Thus, single substrate devices operating as ultrasound devices (e.g., for ultrasound imaging and/or high intensity focused ultrasound (HIFU)) are achieved.

In at least some embodiments, the processes may be reliable (e.g., characterized by high yield and/or high device reliability), scalable to large quantities, and relatively inexpensive to perform, thus contributing to a commercially practical fabrication process for CUTs. The use of complex and costly processing techniques such as the formation of TSVs, the use of CMP, and the use of densification anneals of low temperature oxide bonds may be avoided. Moreover, the processes may provide for the fabrication of small ultrasound devices, facilitating the creation of portable ultrasound probes.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

As a non-limiting example, various embodiments have been described as including CMUTs. In alternative embodiments, PMUTs may be used instead of, or in addition to, CMUTs.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method, comprising:
    forming a plurality of cavities in a layer of silicon oxide on a first side of a first wafer, the first wafer having a second side opposite the first side;
    bonding a second wafer with the first wafer such that the second wafer seals the plurality of cavities in the layer of silicon oxide;
    annealing the first wafer and the second wafer after bonding them together the annealing utilizing a first temperature;
    thinning the first wafer or the second wafer after the annealing to create a thinned wafer;
    etching a plurality of trenches in the thinned wafer, the plurality of trenches defining a plurality of electrode regions of the thinned wafer;
    filling the plurality of trenches in the thinned wafer with an insulating material;
    forming metal contacts on the plurality of electrode regions of the thinned wafer;
    aligning the thinned wafer with an integrated circuit wafer having integrated circuitry formed therein;
    bonding the thinned wafer with the integrated circuit wafer having integrated circuitry formed therein using the metal contacts on the thinned wafer to contact bonding points on the integrated circuit wafer, wherein bonding the thinned wafer with the integrated circuit wafer is performed at a second temperature less than the first temperature; and
    forming a flexible membrane by thinning, after bonding the thinned wafer with the integrated circuit wafer, the first wafer or the second wafer, whichever was not previously thinned as part of forming the thinned wafer.

2. The method of claim 1, wherein the first wafer is a bulk silicon wafer, and wherein thinning the first wafer or the second wafer after the annealing to create a thinned wafer comprises thinning the first wafer from the second side of the first wafer.

3. The method of claim 2, wherein thinning the first wafer from the second side of the first wafer comprises using a timed etch.

4. The method of claim 2, wherein the first wafer comprises a doped silicon layer proximate the first side, and wherein thinning the first wafer from the second side of the first wafer comprises thinning the first wafer to the doped silicon layer.

5. The method of claim 2, wherein the second wafer is a silicon-on-insulator (SOI) wafer, and wherein thinning, after bonding the thinned wafer with the integrated circuit wafer, the first wafer or the second wafer, whichever was not previously thinned as part of forming the thinned wafer, comprises thinning the SOI wafer by removing a handle layer of the SOI wafer.

6. The method of claim 1, wherein the second wafer is a bulk silicon wafer, and wherein thinning the first wafer or the second wafer after the annealing to create a thinned wafer comprises thinning the second wafer.

7. The method of claim 6, wherein the first wafer is a silicon-on-insulator (SOI) wafer, and wherein thinning, after bonding the thinned wafer with the integrated circuit wafer, the first wafer or the second wafer, whichever was not previously thinned as part of forming the thinned wafer, comprises thinning the SOI wafer by removing a handle layer of the SOI wafer.

8. The method of claim 1, wherein the first wafer is a silicon-on-insulator (SOI) wafer, and wherein thinning the first wafer or the second wafer after the annealing to create a thinned wafer comprises thinning the SOI wafer by removing a handle layer of the SOI wafer.

9. The method of claim 8, wherein the second wafer is a SOI wafer, and wherein thinning, after bonding the thinned wafer with the integrated circuit wafer, the first wafer or the second wafer, whichever was not previously thinned as part of forming the thinned wafer, comprises thinning the second wafer by removing a handle layer of the second wafer.

10. The method of claim 1, wherein the method does not involve forming a thru-silicon via (TSV).

11. The method of claim 1, wherein the method does not involve the use of chemical mechanical polishing (CMP).

12. The method of claim 1, wherein the first temperature is less than 1,500 ° C.

13. The method of claim 1, further comprising forming an embedded via in the first wafer or the second wafer, whichever is thinned to create the thinned wafer.

14. The method of claim 13, wherein the embedded via provides electrical connection between the integrated circuitry and the first wafer or the second wafer, whichever was not thinned as part of forming the thinned wafer.

15. The method of claim 13, wherein forming the embedded via further comprises forming the embedded via to extend through the thinned wafer to contact the first wafer or the second wafer, whichever is not thinned.

16. The method of claim 1, wherein the first temperature is up to three times greater than the second temperature.

* * * * *